(12) United States Patent
Dutkiewicz et al.

(10) Patent No.: US 6,329,565 B1
(45) Date of Patent: Dec. 11, 2001

(54) ABSORBENT STRUCTURE AND METHOD

(75) Inventors: Jacek K. Dutkiewicz, Cordova, TN (US); Kristin Ann Goerg-Wood, Sherwood, WI (US); Donald Francis Guay, Appleton, WI (US); Michael Franklin Kalmon, Brillion, WI (US); Bernhardt Edward Kressner, Appleton, WI (US); Yong Li, Appleton, WI (US); Jian Oin, Appleton, WI (US); Krzysztof Andrzej Szymonski; Richard Warren Tanzer, both of Neenah, WI (US); Palani Raj Ramaswami Wallajapet, Brookfield, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/464,133

(22) Filed: Dec. 16, 1999

Related U.S. Application Data
(60) Provisional application No. 60/113,583, filed on Dec. 24, 1998.

(51) Int. Cl.[7] ....................................................... A61F 13/15
(52) U.S. Cl. .................... 604/378; 604/385.01; 442/334; 442/352
(58) Field of Search .................................. 604/367, 368, 604/378, 385.01; 442/334, 352

(56) References Cited

U.S. PATENT DOCUMENTS

| | | |
|---|---|---|
| 3,881,490 | 5/1975 | Whitehead et al. . |
| 4,260,443 | 4/1981 | Lindsay et al. . |
| 4,842,594 | 6/1989 | Ness . |
| 4,950,264 | 8/1990 | Osborn, III . |
| 5,009,653 | 4/1991 | Osborn, III . |
| 5,350,370 | 9/1994 | Jackson et al. . |
| 5,669,894 | 9/1997 | Goldman et al. . |
| 5,800,417 | 9/1998 | Goerg-Wood et al. . |
| 5,820,973 | * 10/1998 | Dodge, II et al. ................... 428/212 |
| 5,843,063 | * 12/1998 | Anderson et al. ................... 604/378 |
| 5,843,852 | 12/1998 | Dutkiewicz et al. . |
| 5,879,343 | * 3/1999 | Dodge, II et al. ................... 604/378 |
| 5,994,615 | * 11/1999 | Dodge, II et al. ................... 604/378 |

OTHER PUBLICATIONS

ASTM D 5729–95, "Standard Test Method for Thickness of Nonwoven Fabrics," 3 pp.

* cited by examiner

*Primary Examiner*—Dennis Ruhl
(74) *Attorney, Agent, or Firm*—Douglas G. Glantz; Thomas J. Connelly; Sebastian G. Pugliese, III

(57) ABSTRACT

A composite absorbent structure and method are disclosed including providing a first wicking layer having preferred liquid transport properties in a preferred contact with a second absorbent retention layer. The composite absorbent structure of the present invention provides preferred liquid transport and liquid retention properties. The composite absorbent structure has a first wicking layer in a preferred contact with the second retention layer by a novel intimate contact means effective to achieve a Contact Intimacy Ratio providing the preferred liquid transport and liquid retention functions when the first wicking layer and the second absorbent retention layer are combined together in accordance with the present invention. In one aspect, a bonding agent is used in the present invention in combination with the first wicking layer of wettable fibers and a second retention layer of a hydrogel-forming polymeric material, preferably superabsorbent, to form a composite absorbent structure having the preferred Contact Intimacy Ratio and providing the preferred liquid transport function and the preferred liquid retention function.

20 Claims, 4 Drawing Sheets

$$CIR \equiv \frac{[(\mu_3 - \sigma_3) - (\mu_1 + \sigma_1)] + [(\mu_2 - \sigma_2) - (\mu_3 + \sigma_3)]}{[(\mu_1 - \sigma_1) + (\mu_2 + \sigma_2)]}$$

ABSORBENT STRUCTURE AND METHOD

The application takes priority under 35 U.S.C. §119(e) from Provisional of U.S. patent application Ser. No. 60/113,583, filed Dec. 24, 1998.

BACKGROUND OF THE INVENTION

1. Technical Field

This invention relates to an absorbent structure and method for liquid distribution and retention. In one aspect, this invention relates to a composite absorbent structure and method for liquid distribution and retention in a disposable absorbent product. In one aspect, this invention relates more particularly to a high integrity, thin, multifunctional material for liquid intake, distribution, and retention in a disposable absorbent product.

2. Background

Disposable absorbent products are used extensively for body waste management. These disposable absorbent products employ an absorbent structure or structures to manage body waste effectively. The absorbent structure or structures within the disposable absorbent product must take up and retain the body wash within the absorbent product.

INTRODUCTION TO THE INVENTION

A body waste management absorbent product is insulted with a liquid in a relatively centralized location. By insulted is meant an addition of a body exudate to a target area of the absorbent product. To prevent leakage caused by the presence of more liquid than absorbent capacity in the centralized insult location, there is a need for the absorbent structure to transport the liquid away from the centralized insult location to a more distant location in the absorbent product. The absorbent structure or structures within the absorbent product first must take up the liquid into the absorbent product, then distribute the liquid, and retain the liquid within the absorbent product.

If the distribution of the liquid by the absorbent structure within the absorbent product is not adequate, the efficiency of the absorbent structure's utilization of its capacity will be low.

To overcome problems of poor distribution, commercially available absorbent products often are designed with an excess absolute liquid saturated retention capacity. In this way, the total absorbent capacity of the absorbent product often is not utilized efficiently.

An increase in liquid distribution efficiency by the absorbent structure potentially would provide a drier absorbent product, e.g., a drier diaper, together with improved aesthetics of appearance of the absorbent product in use.

An increase in liquid distribution efficiency by the absorbent structure potentially would allow either a higher realized liquid saturation level for an absorbent product using the same amount of absorbent structure or the use of less absolute capacity to achieve the same realized liquid saturation level in the absorbent product without any increase in liquid leakage. The use of less absorbent structure to achieve the same realized liquid saturation level in an absorbent product would result in less absorbent product being disposed to the environment.

There is a need therefore to produce an absorbent structure able to exceed the liquid transport properties of known absorbent structures. There is a need also to produce an absorbent structure capable of quickly transporting liquid from a centralized insult location to a preferred, more distant location within the absorbent product.

It is an object of the present invention to provide an absorbent structure and method for liquid distribution and retention.

It is a further object of the present invention to provide a composite absorbent structure and method for use in disposable absorbent products.

It is an object of the present invention to provide a composite absorbent structure and method for use in a thin, disposable absorbent product.

It is an object of the present invention to provide a composite absorbent structure and method for use in a thin, disposable absorbent product, e.g., such as an infant diaper.

It is an object of the present invention to provide a composite absorbent structure and method for use in a disposable absorbent product having a relatively low volume.

It is an object of the present invention to provide a composite absorbent structure and method for use in a disposable absorbent product having a relatively low volume and a relatively high capacity.

It is an object of the present invention to provide a disposable absorbent product including a liquid-permeable top-sheet, a backsheet attached to the topsheet, and an absorbent structure positioned between the topsheet and the backsheet, wherein the absorbent structure provides the composite absorbent structure of the present invention.

These and other objects of the present invention will become more apparent from a review of the figures of the drawings and the detailed description which follow.

SUMMARY OF THE INVENTION

The present invention provides a composite absorbent structure and method including providing a first wicking layer having preferred liquid transport properties in a preferred contact with a second absorbent retention layer. The composite absorbent structure of the present invention provides preferred liquid transport and liquid retention properties. The composite absorbent structure has a first wicking layer in a preferred contact with the second retention layer by a novel intimate contact means effective to achieve a Contact Intimacy Ratio providing the preferred liquid transport and liquid retention functions when the first wicking layer and the second absorbent retention layer are combined together in accordance with the present invention.

In one aspect, a bonding agent is used in the present invention in combination with the first wicking layer of wettable fibers and a second retention layer of a hydrogel-forming polymeric material, preferably superabsorbent, to form a composite absorbent structure having the preferred Contact Intimacy Ratio and providing the preferred liquid transport function and the preferred liquid retention function.

In one aspect, the bonding agent used in the present invention in combination with the first wicking layer and the second retention layer includes sheath/core polyethylene/polypropylene fibers. In one aspect, the bonding agent includes Danaklon sheath/core polyethylene/polypropylene fibers. In one aspect, the bonding agent includes a hydrophilic hot melt adhesive. In one aspect, the bonding agent includes a polyaminoamide epichlorohydrin wet strength resin.

DETAILED DESCRIPTION

Figure 1:
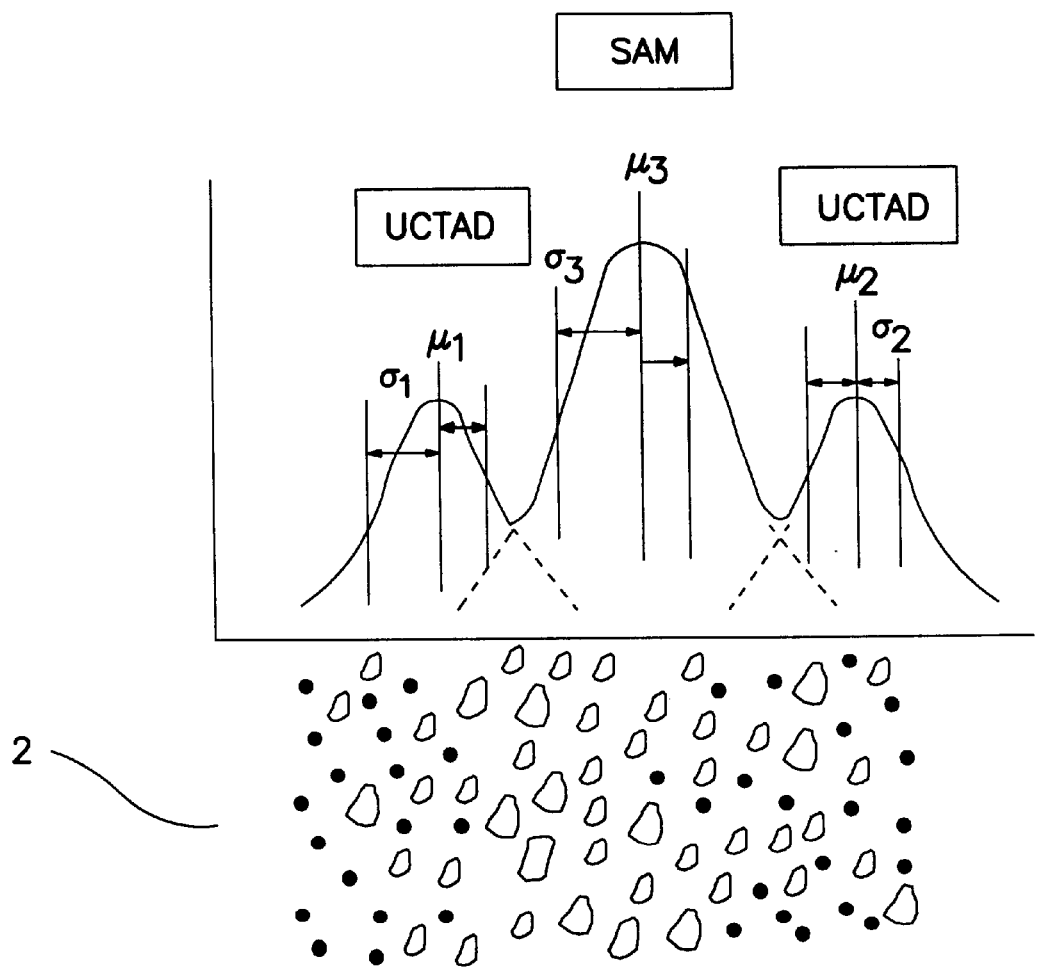
FIG. 1 shows a graphical depiction of Contact Intimacy in accordance with the present invention for a model of a wicking/retention/wicking composite in a projected relationship to the appearance of a cross section of the idealized wicking/retention/wicking composite model.

The absorbent structure and method of the present invention provide a composite absorbent for use in disposable products. The novel composite absorbent structure and method provide a first wicking layer having preferred liquid transport properties in contact with a second retention layer having preferred liquid retention properties.

The absorbent structure and method of the present invention provide a multifunctional absorbent composite (MAC) for liquid intake, distribution, and retention. The multifunctional absorbent material incorporates at least three structural elements for liquid distribution and retention.

In one aspect, the absorbent structure and method of the present invention provide a multifunctional absorbent composite (MAC) for liquid intake, distribution, and retention. The multifunctional absorbent material composite incorporates at least three structural elements for liquid distribution and retention.

A first structural element of the present invention provides an interconnected capillary or channel system (ICS) created by a wettable fibrous network. The fiber network includes a fibrous web capable of uptaking and efficiently spreading or moving the liquid up to a higher elevation.

A second structural element of the present invention provides a retention material including a superabsorbent material (SAM) located in direct physical contact with the interconnected capillary system in such a way that it can receive liquid efficiently from the interconnected capillary system and, by doing so, with subsequent swelling, does not destroy the adjacent capillary system or adversely affect the transfer of liquid to the retention layer. The multifunctional absorbent material structure and method of the present invention attach the super-absorbent material to the surface of the interconnected capillary system. Alternatively, the multifunctional absorbent material structure and method of the present invention embed the super-absorbent material within the interconnected capillary system only on one side of the web leaving the other side substantially free. In any case, a significant portion of the wicking layer is undisturbed by the swelling of the retention material. The superabsorbent material can be used in different physical forms including regular particulates, film, fibers, foam, and the like.

A third structural element of the present invention provides bonds, part of which are water resistant, combining the fibers within the interconnected capillary system and joining the interconnected capillary system with the superabsorbent material. Mechanical, electrical, or chemical means, or combinations of mechanical, electrical, or chemical means are used to create these bonds of the third structural element of the present invention.

The multifunctional material of the present invention provides one integral layer or a plurality of layers placed one upon another. Optionally, the layers can be attached together permanently with mechanical, chemical, or other means.

The multifunctional absorbent structure of the present invention exhibits superior liquid wicking and retention characteristics, thereby providing advantages for use in absorbent personal care products. The multifunctional absorbent structure and method of the present invention have two distinct functionalities, i.e., liquid transport by wicking and liquid retention by absorption. The multifunctional absorbent structure and method of the present invention transport fluid effectively in the absorbent product, have the ability to wick liquid against gravity when the structure is placed in a vertical position, and retains the wicked fluid at a higher location in the structure relative to the point at which liquid contacts the structure.

Absorbent polymeric materials exhibiting liquid retention by absorption are available, but these materials have poor liquid transport properties and, in fact, can impede the transport of fluid by altering the capillary structure essential for liquid transport. Materials for wicking liquid also are available, an example of which are the cellulosic materials UnCreped Through-Air Dried (UCTAD) made by the wet forming approach. However, the absorbent capacity of such liquid transporting materials can be limited, and in some cases, these materials do not serve the preferred liquid retention function of the structure and method of the present invention.

Additionally, the multifunctional absorbent structure and method of the present invention has good mechanical integrity in both the wet and dry state and is thin and flexible for effective use in an absorbent product.

The multifunctional absorbent structure and method of the present invention make a superior multifunctional absorbent structure which combines liquid retention with liquid transport. The multifunctional absorbent structure and method of the present invention combine materials with good liquid retention properties with materials having good liquid transport properties. In one aspect, the multifunctional absorbent structure and method of the present invention combine superabsorbent material with UCTAD materials. To combine these materials and make the absorbent structure, the superabsorbent material of the structure and method of the present invention is combined with the UCTAD material using suitable bonding mechanism. The multifunctional absorbent structure and method of the present invention combine the superabsorbent material and UCTAD in a manner which promotes the effective movement of liquid using the UCTAD layer and transfer of the liquid to the superabsorbent material.

The mechanism of bonding the UCTAD and superabsorbent material in the present invention provides for good wet and dry integrity and does not adversely impact the transfer of liquid from UCTAD to superabsorbent material.

The superabsorbent material remains in contact with UCTAD even after it begins to swell, and the delamination from UCTAD is avoided that would occur because of the large increase in super-absorbent dimensions and the consequent disturbance in bonding between the superabsorbent and UCTAD on swelling. Such a delamination would not only adversely impact the mechanical integrity of the structure but it would also prevent effective transfer of liquid from the UCTAD to the superabsorbent material as the contact between the superabsorbent and UCTAD would be disturbed. The multifunctional absorbent structure and method of the present invention use several approaches to combine the UCTAD and superabsorbent material utilizing physical and chemical forces.

In one aspect, the multifunctional absorbent structure and method of the present invention use a bonding agent to combine the UCTAD and superabsorbent material. The bonding agent used in the multifunctional absorbent structure and method of the present invention maintains the effective contact between the two materials in the dry as well as wet state and also does not adversely impact liquid movement between the two materials. The bonding agent in the present invention has the ability to bond the superabsorbent material to UCTAD and to maintain the bond as the superabsorbent material swells and further allows The multifunctional absorbent structure and method of the present invention liquid transport across the interface formed by the bonding agent between the superabsorbent material and UCTAD.

The multifunctional absorbent structure and method of the present invention were developed empirically. Laminates of UCTAD and superabsorbent materials were made, and the absorbent properties were evaluated. It was found that the desired liquid transport and retention characteristics were obtained only in some specific cases. The multifunctional absorbent structures were examined by a technique using microscopy and image analysis, and the intimacy of contact between the superabsorbent material and UCTAD were found to determine the effectiveness of the absorbent in transporting and retaining liquid.

An example of the multifunctional absorbent laminates formed are laminates of UCTAD and superabsorbent material bonded using Danaklon fibers as the bonding agent. The Danaklon content varies, and the contact between the superabsorbent material and UCTAD is quantified by a parameter termed as the Contact Intimacy Ratio (CIR). The technique to determine the Contact Intimacy Ratio is described in this detailed description herein below. It was found that the CIR has a strong positive correlation to the absorbent performance as measured by the Absorbent Capacity at a height of 15 cm when the absorbent laminate is tested using a absorbent capacity vertical wicking test as described in the methods section. This correlation is clearly observed in comparing the CIR numbers and Absorbent Capacity for samples BK-7 through BK-11 as set forth in the actual Examples described in this detailed description herein below. The correlation coefficient is 0.973. Sample BK-7 is an example of this invention with an Absorbent Capacity of 5.4 g/g, and samples BK-8 through BK-11 have lower absorbent capacity.

In another embodiment of the multifunctional absorbent structure of the present invention, a hydrophilic hot melt adhesive is used to achieve the bonding of the UCTAD to the superabsorbent material and create the multifunctional absorbent structure.

In another embodiment of the multifunctional absorbent structure of the present invention, having an Absorbent Capacity of 7.5 g/g., a water soluble polymer Kymene 557LX is used as the bonding agent, and further used a mixture of superabsorbent and fluff pulp mixture. In this embodiment, the multifunctional absorbent structure is not composed of just the UCTAD layer with SAM and a bonding agent as the other examples. It also has fluff pulp.

The novel multifunctional absorbent structure of the present invention is a laminate composed of (i) a superior liquid transport layer (UCTAD) and (ii) a superior liquid retention material (superabsorbent material) combined together using (iii) a specified bonding agent combined together in a manner which provides both the liquid transport and liquid retention functions found to provide unexpected preferred advantages in the performance of the novel laminate of the present invention.

The novel multifunctional absorbent structure of the present invention is a laminate combined together in a manner to obtain a novel intimate contact to achieve the preferred liquid transport and liquid retention functions.

The multifunctional absorbent structure of the present invention has good wet and dry mechanical integrity and is thin and flexible, thereby providing preferred features for use in absorbent products.

The composite absorbent structure of the present invention provides a first wicking layer including wettable fibers, wherein the first wicking layer exhibits a vertical liquid flux rate value at a height of about 15 centimeters of at least about 0.08 grams of liquid per minute per gram of absorbent structure per meter length of the first wicking layer; a second retention layer including a hydrogel-forming polymeric material; and a bonding agent for bonding the first wicking layer and the second retention layer to form a composite absorbent structure having a minimum contact intimacy ratio for providing a liquid transport function and a liquid retention function such that the first wicking layer and the second retention layer are combined together in a manner to obtain a contact to achieve liquid transport and liquid retention functions at a length of at least about 15 centimeters, a saturated capacity of at least about 5 grams of liquid per gram of composite absorbent structure, and an Absorbent Capacity at 15 cm of at least about 5 grams of liquid per gram of second retention layer. Preferably, the first wicking layer includes wettable cellulosic fibers. Preferably, the first wicking layer includes wettable cellulosic fibers having a wet curl value between about 0.15 to about 0.20. Preferably, the hydrogel-forming polymeric material includes a superabsorbent. In one aspect, the bonding agent includes a sheath/core polyethylene/polypropylene fibers. In one aspect, the bonding agent includes Danaklon fibers. In one aspect, the bonding agent includes a hydrophilic hot melt adhesive. In one aspect, the bonding agent includes a polyaminoamide epichlorohydrin wet strength resin. In one aspect, the first wicking layer exhibits a vertical liquid flux at a height of about 15 centimeters of at least about 0.1 grams, preferably at least about 0.12 grams, of liquid per minute per gram of first wicking layer per meter length of cross-sectional width of the first wicking layer. In one aspect, the first wicking layer exhibits a vertical liquid flux at a height of about 5 centimeters of at least about 0.4 grams, preferably at least about 0.6 grams, of liquid per minute per gram of first wicking layer per meter length of cross-sectional width of the first wicking layer. In one aspect, the the wettable cellulosic fibers exhibit a wet curl value between about 0.11 to about 0.25, the first wicking layer exhibits a vertical liquid flux at a height of about 5 centimeters of at least about 0.4 grams of liquid per minute, the first wicking layer exhibits a wicking time value of less than about 3.5 minutes, and the first wicking layer, having a basis weight of about 200 grams per square meter, exhibits a dry tensile strength at least about 2000 n/m of force per inch of first wicking layer width and a wet tensile strength at least about 200 n/m of force of first wicking layer width, wherein the fibers are present in the first wicking layer in an amount of from about 50 to about 100 weight percent, based on the total weight of the absorbent structure, and the first wicking layer exhibits a density between about 0.08 to about 0.5 grams per cubic centimeter.

In one embodiment of the present invention, the multifunctional material of the present invention material is obtained by providing SAM particles of 25 μm to 300 μm in size, suspended in a stream of air. Alternatively, gravity force also can be used. The SAM particles in air suspension are blown into the sheet. Cellulose fibers are wet-laid using an uncreped through-air dried-type tissue machine. Embedding of SAM particles can be accomplished either at the end of the through-air drying step, or as a separate step on the machine or off the machine.

In the first approach, on the tissue machine, the through-air drier is sectioned such that the last part prior to the sheet leaving the drier provides a slight vacuum (−0.5 to −5 in. (−1 cm to 1 13 cm) of water). The air/SAM suspension is blown into that section.

In the second version, a separate vacuum box is provided after the drier. The material passes above it, and the suspension is blown into the sheet.

In the third version, the SAM embedding takes place during rewinding or converting.

It has been found that the described material is surprisingly thin and flexible.

It has been found that the multifunctional material of the present invention provides very high integrity both in dry and wet conditions.

It has been found that the multifunctional material of the present invention provides surprisingly high efficiency in uptaking, transporting, and permanently locking the fluid, thereby utilizing most of its mass.

It has been found that the multifunctional material of the present invention can be rolled up easily and unwound conveniently for the production of various absorbent articles, e.g., such as sanitary napkins and incontinence devices.

The multifunctional material of the present invention is particularly preferred for making products thinner than currently available absorbent articles containing thick, low-integrity pads of fluff/superabsorbent material composites.

The multifunctional material of the present invention provides for better utilization of the absorbent mass compared to currently available absorbent structures. The increased levels of utilization of the absorbent mass are attributable to a more uniform distribution of liquid within the multifunctional material of the present invention.

Another extremely useful feature of the multifunctional material of the present invention includes a high integrity of the whole absorbent system of the present invention during use in a disposable absorbent product. This integrity is of significant advantage over currently available absorbent articles which have weak absorbent cores.

The present invention provides a multifunctional material combining a liquid distributing function with a liquid retention function. The multifunctional material of the present invention includes preferably a cellulose-based sheet having embedded in it superabsorbent material (SAM) particles.

The multifunctional material of the present invention provides features, on a test basis using liquid of 0.9% sodium chloride, listed as follows.

1. A vertical liquid flux at a height of about 15 centimeters no lower than 0.06 grams of liquid wicked per minute per gram of material per meter of sample length.

2. A saturation of the material at 15 cm elevation (15-cm vertical wicking) no lower than 5 grams of liquid/gram of material after 60 min.

3. A permeability of the material measured horizontally under 0.3 psi mechanical load no lower than 100 Darcy after 60 minutes.

A novel structural analysis method has been developed to be used for the multifunctional composites of the present invention. The method measures "closeness" or intimacy with which layers touch each other. The term "Contact Intimacy Ratio" (CIR) is used to describe the novel development. A pictorial, idealized model of a wicking/retention/wicking composite, e.g., an UCTAD / SAM / UCTAD composite was drawn, and an equation developed. The term "UCTAD" is an acronym for uncreped, through-air dried (UCTAD). The equation also can be used for a two layer wicking/retention composite.

Referring now to FIG. 1, a graphical depiction is shown of the Contact Intimacy for the model of an UCTAD / SAM / UCTAD composite model in a projected relationship to the appearance of a cross section 2 of the idealized model of an UCTAD/SAM/UCTAD composite model.

An embedding and cross-sectioning technique has been developed for analyzing the composite absorbent structures of the present invention.

Software has been written and tested for auto-stage, automatic image analysis of scanned visual images of cross sections of the composite absorbent structures of the present invention.

Parameters from CI have been shown to correlate well (r=0.97) with absorption performance for various particulate composites; and rank appropriately various fibrous SAM composites.

It is preferred that the first wicking layer of the present invention can quickly and effectively transport liquid from a centralized liquid insult location to distant locations within the first wicking layer or within a disposable absorbent product. With such an ability, the first wicking layer of the present invention is particularly useful, for example, as a liquid distribution material within a disposable absorbent product.

Distribution must take place at an acceptable speed such that the target insult area, the crotch area, is ready for the next insult. The time between insults can range from just a few minutes to hours, depending on the age of the wearer.

To achieve a preferred transportation function, a distribution layer must have a high capillary tension value. Capillary tension in distribution and other materials not containing superabsorbents is measured simply by the equilibrium vertical wicking height of an aqueous saline solution containing 9.0 g/l sodium chloride per liter, not by the test method given for materials containing superabsorbents. A successful distribution layer must have a capillary tension greater than the adjacent material from which it receives liquid and preferably a capillary tension of at least about 15 cm. Because of an inverse relationship between capillary tension and permeability, a high capillary tension provides the distribution layer with a low permeability.

In the case of an infant's diaper, for example, it is preferred that about 8 grams of a distribution material having a basis weight of about 200 grams per square meter would be capable of being able to transport about 100 milliliters of liquid, and preferably about 120 milliliters of liquid, within about 30 minutes to a distance of up to about 15 centimeters away from a centralized liquid insult location.

One liquid transport property preferred of the first wicking layer of the present invention is that the first wicking layer exhibits a vertical liquid flux, at a height of about 15 centimeters, preferably of at least about 0.08 grams of liquid per minute per gram per square meter of first wicking layer, more preferably of at least about 0.003 g/(min×gsm×inch), and up to about 0.1 g/(min×gsm×inch). The Vertical Liquid Flux rate can be determined as set forth in the Vertical Liquid Flux rate test procedure as set forth in U.S. Pat. No. 5,843,852 which is hereby incorporated by reference and included herein as if set forth verbatim. The term "g/min*gsm*inch" refers to grams of liquid per minute per gram per square meter of first wicking layer per inch of cross-sectional width of the absorbent structure. As used herein, the Vertical Liquid Flux rate value of a first wicking layer is meant to represent the amount of liquid transported across a boundary a specified vertical distance away from a centralized liquid insult location per minute per normalized quantity of the absorbent structure. The Vertical Liquid Flux rate, at a height of about 15 centimeters, of a first wicking layer may be measured according to the test method described herein.

Another liquid transport property preferred of the first wicking layer of the present invention is that the absorbent structure exhibits a vertical liquid flux, at a height of about 5 centimeters, preferably of at least about 0.01 g/(min×gsm×inch), more preferably of at least about 0.015 g/(min×gsm×inch), most preferably of at least about 0.02 g/(min×gsm×inch), and up to about 0.5 g/(min×gsm×inch). The vertical liquid flux, at a height of about 5 centimeters, of a first wicking layer may be measured according to the test method described herein.

Another liquid transport property preferred of the first wicking layer of the present invention is that the first absorbent layer exhibits a Wicking Time value of a liquid to an elevation of 15 centimeters of preferably less than about 3.5 minutes, more preferably less than about 3 minutes, and most preferably less than about 2.5 minutes. As used herein, the Wicking Time value of an absorbent structure is meant to represent the time needed to transport a liquid a specified vertical distance away from a centralized liquid insult location. The Wicking Time value of a liquid to an elevation of 15 centimeters for a first wicking layer may be measured according to the test method described herein.

The first wicking layer of the present invention should have a density such that the first wicking layer exhibits the preferred liquid transport properties described herein. The density of a first wicking layer determines the porosity, permeability, and capillary structure of the first wicking layer. If the density of the first wicking layer is too high, the capillaries of the first wicking layer will be too small such that the capillaries provide a relatively high capillary tension force but, because of the relatively small capillaries, the permeability of the first wicking layer will be relatively low. If the permeability of the first wicking layer is relatively low, the first wicking layer will transport only relatively small amounts of liquid so that the vertical liquid flux rate of the first wicking layer is relatively low at each of about 5 centimeters and of about 15 centimeters of height from a source of liquid.

If the density of the first wicking layer is too low, the permeability of the first wicking layer is relatively high. The capillaries of the first wicking layer are relatively large such that the capillaries provide relatively low capillary tension force providing the first wicking layer is unable to transport liquid quickly to relatively high elevations such as about 15 centimeters of height from a source of liquid. Such a first wicking layer has a relatively high vertical liquid flux rate at a height of about 5 centimeters of height from a source of liquid, but the liquid will move slower and slower, or stop altogether, the higher the front of the wicked liquid. The vertical liquid flux rate of the first wicking layer is relatively low at about 15 centimeters of height from a source of liquid.

Depending on the stability of the capillary structure of a first wicking layer, the density of the first wicking layer may change as a liquid enters into the capillary structure of the first wicking layer. The structural stability of the first wicking layer depends on such factors as the stability, as measured by shape, curl, stiffness, or resiliency, of the fibers in the first wicking layer as well as the stability of the first wicking layer as a whole. Structural changes of the first wicking layer are more likely if the first wicking layer is under a stress or pressure as, for example, when the first wicking layer is used in a diaper being worn by a human.

It is preferred that the density of the first wicking layer does not change substantially when the first wicking layer absorbs a liquid or otherwise becomes wet or is under a stress or pressure and/or that the first wicking layer substantially recovers its density after the liquid or stress or pressure is removed from the absorbent structure. The stability of the density of the first wicking layer may be quantified by the difference in densities exhibited by the first wicking layer when different loads, such as each of loads of about 1000 Pa to 2000 Pa, are applied to the first wicking layer. If the difference in the densities exhibited by the first wicking layer at the different loads is relatively small, the first wicking layer is considered to be structurally stable. Another method of characterizing the structure of a first wicking layer is by measuring the void volume of the first wicking layer. The first wicking layer has a basis weight of from about 35 to about 300 gsm, or more preferably from about 80 to about 200 gsm, a density of between about 0.08 and about 0.5 g/cc, and a permeability between about 50 and about 1000 Darcys.

It is preferred to use little first wicking layer in the disposable absorbent product, and preferably the first wicking layer of the present invention exhibits a total weight less than a certain number of grams, e.g., depending on the particular disposable absorbent product.

The first wicking layer of the present invention should exhibit sufficient dry and wet tensile strengths such that the first wicking layer maintains its structural integrity during manufacturing, handling, and use. The dry and wet tensile strengths of wet-laid first wicking layers are provided for a first wicking layer of the present invention. It is preferred that a first wicking layer of the present invention, having a basis weight of about 200 grams per square meter, exhibits a dry tensile strength at least about 2000 N/m of force of first wicking layer width, preferably at least about 3000 N/m of force per inch of first wicking layer width, and more preferably at least about 4000 N/m of force per inch of first wicking layer width. It is preferred that a first wicking layer of the present invention exhibits a wet tensile strength at least about 200 N/m of force of first wicking layer width, preferably at least about 400 N/m of force of first wicking layer width, and more preferably at least about 800 N/m of force of first wicking layer width.

In one embodiment, a wet strength resin is added to the fibers forming a first wicking layer to improve the wet strength properties of the first wicking layer. The wet strength resin is sufficiently hydrophilic so that the resin does not adversely affect the wettability of the fibers.

In one embodiment, the first wicking layers of the present invention are prepared by a wet-laying process. The wet laying process provides a first wicking layer which exhibits sufficient dry and wet tensile strengths. In contrast, an air-laying process results in a first wicking layer that will not exhibit sufficient dry and wet tensile strengths. However, by using wet strength resins, binder fibers, or by the careful selection of fibers used to prepare the first wicking layer, an air-laid first wicking layer is prepared that exhibits the properties preferred in the present invention.

Binder fibers can be used in the present invention.

Preferably, the process used to prepare the first wicking layer is an uncreped, through-air dried (UCTAD) process. The uncreped, through-air dried (UCTAD) process is set forth in U.S. Pat. No. 5,843,852 which is hereby incorporated by reference and included herein as if set forth ver batim.

It has also been discovered that the liquid transport properties of a first wicking layer of the present invention may be improved if the first wicking layer is a composite including multiple layers or sections of separate first wicking layers as compared to a unitary absorbent structure. As such, instead of preparing a unitary absorbent structure of a particular size or dimension, it may be desirable to prepare separate absorbent structure layers or sections that, when attached or combined with each other, form a composite that is substantially the same size and/or dimensions as the unitary absorbent structure. As an example, instead of preparing a unitary absorbent structure having a basis weight of about 200 grams per square meter, it may be desirable to prepare four separate absorbent structure layers each having a basis weight of about 50 grams per square meter. If effectively attached or combined with each other, the four smaller absorbent structure layers will form a composite that has a basis weight of about 200 grams per square meter and otherwise substantially has the same size and/or dimensions as the unitary absorbent structure.

The novel Contact Intimacy method to measure structure in UCTAD/SAM Composites includes a structural analysis method specific to UCTAD/SAM composites. The method successfully correlates with 15-cm vertical absorption capacity on UCTAD/SAM samples and ranks the fibrous SAM composites appropriately.

FIG. 1 shows an original concept diagram and equation for normalized Contact Intimacy using means and standard deviation of a location histogram (X-coordinates) within each field of view. The FIG. 1 equation represents only one form that applies to the geometry of UCTAD / SAM / UCTAD. The equation is modified to accommodate UCTAD / UCTAD / SAM, or just UCTAD / SAM.

A plot of 4-cm Absorption Capacity, as the Y-variable, versus the standard deviation in SAP location as the X-(independent) variable results in a correlation coefficient (0.97) which is actually negative, revealing an inverse trend such that absorption physically is better when SAM particles are more closely spaced or closer together. The more positive the CI value, the better the intermixing, and hence, the better the intimacy of contact.

The preparatory method for the cross-sections now will be described. Calco Oil Red YM liquid dye (BASF, New Jersey, USA) was used to counter-stain the medium, thereby to provide an intermediate shade of gray for image analysis.

The following procedure provides for embedding and microtomy of superabsorbent particle—tissue composites for light microscopy.

1. Cut out a segment of sample to fit within 1 to 2 millimeters of the mold dimensions. The mold size and design should be such that the final 15 $\mu$m thin section is 1 cm wide by at least 4 cm long with the sample reasonably centered in the cross-section. For example, the mold can be a rectangular clear polystyrene container [inside dimensions=30 mm (W)×72 mm (L)×12 mm (H)], and the cut sample dimensions can be 29 mm×70 mm.

2. Glue a 3 mm thick [60mm (L)×13 mm (W)] plastic spacer to the bottom, center of the mold to keep samples from settling to the bottom of the mold. Do not use wood splints which tend to out-gas and release air bubbles which float up into the sample.

3. Epofix (Struers, Copenhagen, DM) epoxy preparation:
   A. Dispense 30 grams of resin into a disposable container.
   B. Add 6 drops of Calco oil red YM liquid (BASF, New Jersey, USA). Dye is added to the resin to give the final thin section an optical density intermediate between the pulp fibers which are darker and the superabsorbent particles which are brighter.
   C. Mix thoroughly for 2 minutes.
   D. Place under vacuum for at least 1 hour to de-gas the resin.
   E. Add 3.6 grams hardener (ratio by weight=8.33:1 R:H).
   F. Mix thoroughly for 2 minutes.
   G. Pour part of mixture into mold to 3/4 full and place mold and remaining epoxy under vacuum for no longer than 15 minutes. Mixed epoxy has a pot life of about 30 minute before it thickens significantly.
   H. Gently lower sample into epoxy and let it fully saturate.
   I. Add extra epoxy around the edges of the sample until fully saturated and completely covered.
   J. Let sample set at room temperature overnight for complete curing.

4. Trim the cured block by cutting off a 5 mm thickness from the four sides and ends to expose the embedded sample and ensure any compressed edges of the sample compressed by trimming with scissors have been removed.

5. Trim away the base of the mold to remove the polystyrene layer, as this will interfere with cutting undistorted sections in the microtome.

In steps 4 & 5, best results were obtained by cutting with a band saw followed by flattening the cut with a belt sander.

6. A block is produced having dimensions of 2 cm (W)×6 cm (L)×1 cm (H). Two thin-section samples are obtained from each block by cutting the two opposing 1 cm×6 cm faces with the microtome.

7. Microtomy of the block faces.
   A 40° tungsten carbide knife set at the zero (recommended) position was used.
   A. Mount block face securely with the longest dimension parallel to the direction of travel.
   B. Plane off the block face at 50 $\mu$m per pass and no more than 3 mm per second until entire surface is flat.
   C. Remove 4 additional sections at 15 $\mu$m per pass and 1.5 mm per second. Huffing the block face with a few short breaths prior to each pass will soften the superabsorbent particles (SAP) sufficiently to prevent them from fracturing when cut. Too much softening will compress the particles upon cutting, forming adjacent holes.
   D. Repeat with the fifth section and hold the leading edge of the section taut with tweezers as it comes off to avoid wrinkling and curling.

8. Mounting thin-sections for microscopy and image analysis:
   A. Place flat on a clean, dry microscope slide (1"×3" are preferred) and trim off the leading and trailing ends with a razor blade.

B. Reposition the trimmed thin-section on the center of the slide in three drops of refractive index liquid (R.I.=1.572 from R. P. Cargille Laboratories, Inc., Cedar Grove, N.J.). Place two additional drops on top of the section.

C. Work out any trapped air bubbles with a clean, smooth probe while viewing under a low power stereomicroscope.

D. Cover with a 50 mm to 60 mm No. 1½ cover glass.

In the procedure for analyzing Contact Intimacy, the sample is illuminated by four low-angle incident flood lamps. The sample then is imaged with a 20 mm Leica Quantimet 970 Image Chalnicon scanner and a Leica Quantimet 970 Image Analysis System (Leica Corp., Deerfield Ill.)

A software routine for the Quantimet 970 Image Analysis System has been developed to automate the Contact Intimacy analysis. The routine "CONIM8" provides auto-stage motion from field to field, centering of the image within each field, and data extraction from location histograms to calculate several versions of Contact Intimacy. Optical and imaging conditions are listed directly as follows.

Cambridge Instruments QUANTIMET 970 QUIPS/MX: V08.00 USER:
ROUTINE: CONIM7 DATE: RUN: SPECIMEN:
NAME = CONIM7
DOES = SCANS SLIDE TO GET CONTACT INTIMACY OF SAM/UCTAD X-SECTNS.
BUT SLIDE IS POSITIONED BY ST6 ON LEFT UCTAD LAYER, AND REGIONS ARE CHOSEN MANUALLY. ALSO GETS THE ABS CONTIN PER LAYER, AS POST-ANALYSIS CALC.
AUTH = B.E. KRESSHER /
DATE = JUL. 2, 1997
COND = 2X OBJ ON OLYMP SCOPE; TRANS LIGHT; VHDF; LOW-MAG CONDENS SCANNER ROATED 90 DEG COUNTER-CLOCKWISE; IM AMP AT 1.0
Enter Specimen Identity
Scanner (No. 2 Chalnicon LV = 3.99 SENS= 1.46 PAUSE)
Calibrate User Specified (Cal Value = 9.135 microns per pixel) SUBRTN STANDARD
Load Shadinq Corrector (pattern-CONIM3)

```
CONTIM      := 0.
TOTFIELD5   := 0.
LAYERS      := 1.
LAYERS      := 1.
HCOUNT      := 0.
HMEAN       := 0.
HSO         := 0.
HMEDIAN     := 0.
HSKEW       := 10.
STGPERPX    := 10.
A           := 140.
A           := 250.
For SLIDE = 1 to 1
STAGEX      := 5000.
STAGEY      := 10000.
Stage Move  (STAGEX,STAGEY)
Staqe Scan  (  X      Y
   Scan oriqin   STAGEX   STAGEY
   Field size    3800.0   2000.0
   No of fields  15       1      )
FLAG        := 3.
Pause message
PLEASE POSITION THE SLIDE FOR ANALYSIS
Pause
For FIELD
```

Image Frame is Rectangle ( X: 48, Y: 187, W: 800, H: 324, )
Pause Message
DETECT LEFT FIBERS FOR STGE POSITIONIN6
Detect 2D ( Darker than 46, Delin PAUSE )
Amend ( OPEN by 1—Horizontally )
Edit (pause) EDIT
Amend ( CLOSE by 20)
Measure feature AREA X.FCP Y.FCP XCENTROID into array FEATURE ( of 1000 features and 5 parameters )

```
HMEAN := Field sum of FEATURE XCENTROID
If HMEAN > A then
DISTANCE   := ( HMEAN – A ) % STGPERPX
STAGEY     := STAGEY – DISTANCE
Stage move ( STAGEX,STAGEY)
Else
DISTANCE   := ( A – HMEAN ) % STGPERPX
STAGEY     := STAGEY + DISTANCE
Stage Move ( STAGEX,STAGEY)
Endif
```

Pause message
PLEASE DETECT SAM PARTICLES
Detect 2D ( Lighter than 58, Delin PAUSE )
Amend ( CLOSE by 1)
Amend ( OPEN by 1)
Amend ( CLOSE by 2)
Pause Message
SELECT OTHER SAM, AND REMOVE DEBRIS . . .
Edit (pause) EDIT

```
Measure feature   AREA   X.FCP   Y.FCP   XCENTROID
      into array FEATURE ( of 1000 features and 5 parameters )
FEATURE XCENTROID := XCENTROID % CAL.CONST
```

Distribution of COUNT v XCENTROID (Units MICRONS ) from FEATURE in HIST03 from 0. to 7700. in 14 bins (LIN)
Pause Message
DETECT LEFT-SIDE FIBER LAYER (U1, S1) . . .
Detect 20 ( Darker than 48, Delin PAUSE )
Amend ( OPEN by 1—Horizontally )
Pause message
SELECT LEFT-SIDE FIBER REGION . . .
Edit (pause) EDIT

```
Measure feature   AREA   X.FCP   Y.FCP   XCENTROID
      into array FEATURE ( of 1000 features and 5 parameters )
FEATURE XCENTROID := XCENTROID % CAL.CONST
```

Distribution of COUNT v XCENTROID (Units MICRONS ) from FEATURE in HIST01 from 0. to 7700. in 14 bins (LIN)
If LAYERS = 2, then
Pause Message
DETECT RIGHT-SIDE FIBER LAYER (U2, S2) . . .
Detect 20 ( Darker than 48, Delin PAUSE )
Amend ( OPEN by 1—Horizontally )

Pause message
SELECT RIGHT-SIDE FIBER REGION . . .
   Edit (pause)

---

Measure feature   AREA   X.FCP   Y.FCP   XCENTROID
   into array FEATURE ( of 1000 features and 5 parameters )
FEATURE XCENTROID := XCENTROID % CAL.CONST

---

Distribution of COUNT v XCENTROID (Units MICRONS ) from FEATURE in HIST02 from 0. to 7700. in 14 bins (LIN)
   Endif
TOTFIELDS := TOTFIELDS + 1.
   Stage Step
   Pause Message
DO YOU WANT TO CONTINUE?. . .
   Pause
   Next FIELD
   Next

---

Special Function # 5 : READ STATISTICS FROM HISTOGRAMS
HMEAN3         := HMEAN
HSD3           := HSD
SAMMINUS       := HMEAN3 − HSD3
SANPLUS        := HMEAN3 + HSD3
FLAG3          := 1.
Special Function # 5 : READ STATISTICS FROM HISTOGRAMS
HMEAN1         := HMEAN
HSD1           := HSD
LEFTMINUS      := HMEAN1 − HSD1
LEFTPLUS       := HNEAM1 + HSD1
If LAYERS = 2. then
FLAG3          := 2.
Special Function # 5 : READ STATISTICS FROM HISTOGRAMS
HMEAN2         := HMEAN
HSD2           := HSD
RITEMINUS      := HMEAN2 − HSD2
RITEPLUS       := HNEAM2 + HSD2
Endif
NUMERAIR       := ( SAMMINUS − LEFTPLUS ) +
                  ( RITEMINUS − SAMPLUS )
NUMERATR       := SAMMINUS − LEFTPLUS
DENOMIN        := ( LEFTMINUS + RITEPLUS )
DENOMIN        := LEFTMINUS + SAMPLUS
CONTIM         := ( − 10. ) % NUMERATR / DENOMIN Print " "
Print "TOTFIELDS =" , TOTFIELDS , "OF HE16HT=" , I.FRAME.H %
CAL.CONST
Print " "
Print "CONTACT INTIMACY RATIO =" , CONTIM , " (MORE POSITIVE = BETTER ) "
Print " "
Print "ABS CONTACT INTIMACY { ) =" , NUMERATR , " (MORE NEGATIVE= BETTER)"
Print " "
Print "CONTIM / INTERFACE PAIR () =" , NUMERATR / LAYERS, "(SMALLER-BETTER)
Print " "
Print " "
Print "CENTERING DISTANCE (pixels) =", A
Print " "
Print " "
Print Distribution ( HIST03, differential, bar chart, scale = 0.00)
Print "DISTRIB OF SAM LOCATION ()"
For LOOPCOUNT = 1 to 24
Print " "
Next
Print Distribution ( HISTO1, differential, bar chart, scale = 0.00 )
Print "DISTRIB OF LEFT UCTAD LAYER ()"
Print " "
Print " "
Print " "
If LAYERS = 2. then
Print Distribution ( HIST02, differential, bar chart, scale = 0.00 )
Print "DISTRIB OF RIGHT UCTAD LAYER ($\mu$m)"
Endif
For LOOPCOUNT = 1 to 35
Print
Next
END OF PROGRAM The procedure for Absorbent Capacity is described herein below under the Test Method identified as "Absorbent Capacity Vertical Wicking Test." In the Absorbent Capacity Test procedure, the amount of fluid in a 4 cm slice that is 13–17 cm above the fluid reservoir level is measured as an indicator of wicking performance of the UCTAD / SAM composites of the present invention. See FIG. 7.

In one aspect, the present invention includes a composite absorbent structure providing a first wicking layer having preferred liquid transport properties in contact with a second retention layer having preferred liquid retention properties.

The second retention layer includes a hydrogel-forming polymeric material and exhibits an Absorbent Capacity at 15 centimeters of at least about 5 grams of liquid per gram of second retention layer.

In one aspect the second retention layer includes a superabsorbent material (SAM). By superabsorbent material is meant a polymer having an absorbent capacity of at least 10 grams of 0.9% by weight of aqueous sodium chloride solution per gram of polymer.

As used herein, the term "superabsorbent material" refers to a water-swellable, water-insoluble organic or inorganic material having an absorbent capacity of at least 10 grams of 0.9% by weight of aqueous sodium chloride solution per gram of polymer and capable of absorbing at least about 20 times its weight and, preferably, at least about 30 times its weight in an aqueous solution containing 0.9 weight percent of sodium chloride. Organic materials suitable for use as a superabsorbent material of the present invention can include natural materials such as agar, pectin, guar gum, and the like, as well as synthetic materials such as synthetic hydrogel polymers. Such hydrogel polymers include, for example, alkali metal salts of polyacrylic acids, polyacrylamides, polyvinyl alcohol, ethylene maleic anhydride copolymers, polyvinyl ethers, hydroxypropyl cellulose, polyvinylmorpholinone, and polymers and copolymers of vinyl sulfonic acid, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers preferably are lightly crosslinked to render the material substantially water insoluble. Crosslinking may be by irradiation, or by covalent, ionic, Van der Waals, or hydrogen bonding. Preferred superabsorbent materials are shell crosslinked so that the outer surface or shell of the super-absorbent particle, fiber, flake, film, foam, or sphere possesses a higher crosslink density than the inner portion of the superabsorbent. The superabsorbent materials may be in any form suitable for use in absorbent composites including particles, fibers, flakes, films, foams, or spheres. In one preferred embodiment of the present invention, the superabsorbent material includes particles of hydrocolloids, preferably an ionic hydrocolloid.

An example of superabsorbent material polymer suitable for use in the present invention is SANWET ASAP 2300 polymer available from Chemdal, a business having offices in Portsmouth, Va. Other suitable superabsorbents may include DOW DRYTECH 2035LD polymer obtained from Dow Chemical Co., a business having offices in Midland, Mich.; or FAVOR SAB 870M and FAVOR SAB 880 polymer available from Stockhausen, Inc., a business having offices in Greensboro, N.C.

As used herein, the term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

A wide variety of fibers are employed in the preparation of the first wicking layer of the present invention. Illustrative fibers include, but are not limited to, cellulosic fibers such as wood and wood products, e.g., wood pulp fibers; non-woody paper-making fibers from cotton, from straws and grasses, such as rice and esparto, from canes and reeds, such as bagasse, from bamboos, from stalks with bast fibers, such as jute, flax, kenaf, cannabis, linen and ramie, and from leaf fibers, such as abaca and sisal; and man-made fibers obtained from regenerated cellulose or cellulose derivatives, such as cellulose acetate. The first wicking layer of the present invention also can use mixtures of such materials, e.g., mixtures of one or more cellulosic fibers.

Other materials from which the first wicking layer may be made include non-cellulosic fibers such as wool, glass, or silk, synthetic fibers, woven fabrics, and nonwoven webs. For example, the distribution layer may be a nonwoven fabric layer composed of a meltblown or spunbond web of polyolefin filaments. Such nonwoven fabric layers may include conjugate, biconstituent, and homopolymer fibers of staple or other lengths and mixtures of such fibers with other types of fibers. The first wicking layer also can be a bonded carded web, an airlaid web, a wetlaid pulp structure composed of natural or synthetic fibers, or a combination of a bonded carded web, an airlaid web or a wetlaid pulp structure composed of natural or synthetic fibers.

In one embodiment of the present invention, it is preferred that the fibers used to prepare a first wicking layer be wettable. As used herein, the term "wettable" is meant to refer to a fiber or material which exhibits a water in air contact angle of less than 90°, i.e., 0° to 90°. Preferably, the cellulosic fibers useful in the present invention exhibit a water in air contact angle between about 0° to about 50° and more preferably between about 0° to about 30°. Preferably, a wettable fiber refers to a fiber which exhibits a water in air contact angle of less than 90°, at a temperature between about 0° C. and about 100° C., and preferably at typical in-use conditions, such as about 20° C. to 40° C.

Suitable fibers are those which are naturally wettable. However, naturally nonwettable fibers also can be used. It is possible to treat the fiber surfaces by an appropriate method to render them more or less wettable. When surface-treated fibers are employed, the surface treatment is nonfugitive; that is, the surface treatment does not wash off the surface of the fiber with the first liquid insult or contact. A surface treatment on a nonwettable fiber is considered to be nonfugitive when a majority of the fibers demonstrate a water in air contact angle of less than 90° for three consecutive contact angle measurements, with drying between each measurement. When the same fiber is subjected to three separate contact angle determinations, and when all three of the contact angle determinations indicate a contact angle of water in air of less than 90°, the surface treatment on the fiber will be considered to be nonfugitive. When the surface treatment is fugitive, the surface treatment will wash off from the fiber during the first contact angle measurement, exposing the nonwettable surface of the underlying fiber, and will demonstrate subsequent contact angle measurements greater than 90°.

Beneficial wettability agents include polyalkylene glycols, such as polyethylene glycols. The wettability agent is used in an amount less than about 5 weight percent, preferably less than about 3 weight percent, and more preferably less than about 2 weight percent, of the total weight of the fiber, material, or absorbent structure being treated.

The fibers are present in the first wicking layer of the present invention in an amount effective to result in the first wicking layer being able to transport a preferred amount of liquid under preferred conditions. The fibers are present in the first wicking layer of the present invention in an amount of from about 30 to about 100 weight percent, preferably from about 50 to about 90 weight percent, and more preferably from about 70 to about 90 weight percent, based on the total weight of the absorbent structure.

During processing or preparation, a cellulosic fiber often has a curl imparted to it such that the fiber is no longer straight and becomes shortened. Such a curl may be the result of either chemical or mechanical means. The curl of a fiber may be quantified by a curl value which measures the fractional shortening of a fiber because of kink, twists, bends, or a combination of kink, twists, and bends in the fiber. For the purposes of this invention, a fiber's curl value is measured in terms of a two dimensional plane, determined by viewing the fiber in a two dimensional plane. To determine the curl value of a fiber, the projected length of a fiber as the longest dimension of a two dimensional rectangle encompassing the fiber, F, and the actual length of the fiber, L, are both measured. An image analysis method may be used to measure L and F. A suitable image analysis method is described in U.S. Pat. No. 4,898,642, incorporated herein in its entirety by reference. The curl value of a fiber can then be calculated from the following equation:

$$\text{Curl Value} = (L/F) - 1 \qquad \text{(Eq.1)}$$

Depending on the nature of the curl of a cellulosic fiber, such curl may be stable when the cellulosic fiber is dry but may be unstable when the cellulosic fiber is wet.

The cellulosic fibers useful in preparing the first wicking layers of the present invention have been found to exhibit a substantially stable fiber curl when wet. This property of the cellulosic fibers may be quantified by a Wet Curl value, as measured according to the test method described herein, which is a length weighted mean curl, averaged over a designated number of fibers, such as about 4000, from a fiber sample. As such, the Wet Curl value is the summation of the individual wet curl values for each fiber multiplied by the fiber's actual length, L, divided by the summation of the actual lengths of the fibers. The Wet Curl value is calculated by only using the necessary values for those fibers with a length of greater than about 0.4 millimeter.

The cellulosic fibers useful in preparing the first absorbent layers of the present invention have been found to exhibit a Wet Curl value preferably between about 0.11 to about 0.25, more preferably between about 0.13 to about 0.22, and most preferably between about 0.15 to about 0.20. Cellulosic fibers exhibiting a suitable Wet Curl value have been found to result in a first wicking layer exhibiting the preferred liquid transport properties. In contrast, cellulosic fibers not exhibiting a suitable Wet Curl value have been found not to result in a first wicking layer exhibiting the preferred liquid transport properties. As such, the Wet Curl value of a cellulosic fiber may be used to determine if the cellulosic fiber will be capable of being used to prepare a first wicking layer having the preferred liquid transport properties described herein.

If a mixture of two or more cellulosic fibers is used to prepare the first wicking layer of the present invention, the mixture of fibers should exhibit a Wet Curl value preferably between about 0.11 to about 0.25, more preferably between about 0.13 to about 0.22, and most preferably between about 0.15 to about 0.20.

Stiffer fibers preserve their shape, including curl, better in water than fibers which are not stiff. As such, stiffer fibers maintain the porosity of a first wicking layer when wet, thus making the wet first wicking layer more permeable to liquid. In addition, resiliency of the fibers is an advantage if the first wicking layer is exposed to any stresses. Resiliency of a fiber aids the fiber in recovering its original shape and the porous structure of the first wicking layer when the stress is removed. Such features are advantageous for maintaining the liquid transport properties of the absorbent structure.

The stiffness and resiliency of fibers are improved by crosslinking the fibers, e.g., such as by oxidation, sulfonation, heat treatment, irradiation, chemical crosslinkers, or by sizing the fibers with polymers such as starch or chitosan; by changing the supermolecular structure of the fiber, e.g., such as by treating the fiber with swelling agents, such as alkaline solutions, and subsequently deswelling the fiber; or by fractionating the source of the fibers so as to obtain pulp containing, for example, a higher amount of coarser, stiffer fibers, such as latewood fibers from wood sources.

A stiffer fiber may require less curl to be useful in the present invention. For example, coarse latewood fibers often have a relatively low Wet Curl value. Yet, a first wicking layer prepared from a latewood-rich fraction from a softwood kraft may possess effective porosity, permeability, and density to exhibit preferred Vertical Liquid Flux rate values.

In one embodiment of the present invention, a source of fiber is fractionated to obtain fibers having preferred properties.

The presence of very small fiber, or fines, in the cellulosic fibers useful in preparing the first wicking layer of the present invention have been found to exhibit a negative effect on the liquid transport performance of the first wicking layer. As used herein, the term "fines" is intended to refer to very small fibers that have a length that is less than about 0.2 millimeter. The weight percent of fines in a fiber sample may be determined by using a fiber analyzer instrument such as the Fiber Quality Analyzer, OpTest Product Code DA93, available from OpTest Equipment Inc., Hawkesbury, Ontario, Canada, the same equipment used herein to measure the Wet Curl value of a fiber sample. It is believed that such fines decrease the porosity of the first wicking layer and retard the transport of liquid. As such, it is preferred that the amount of fines present in a first wicking layer of the present invention be minimized as much as possible. The weight percent of fines in a fiber sample is less then about 4, preferably less than about 2, and more preferably less than about 1 weight percent of the total weight of fibers in the fiber sample.

The cellulose fibers useful in preparing the first wicking layer of the present invention may be prepared by mechanical, chemical, and thermal processes, and by combinations of mechanical, chemical, and thermal processes. Such methods are suitable as long as such methods result in the cellulose fibers exhibiting the properties described herein so that the first wicking layer prepared using such fibers exhibits the preferred liquid transport properties described herein.

One method of preparing the cellulose fibers useful in the present invention is to sulfonate the fibers. Such a process is described in U.S. Pat. No. 5,522,967, issued Jun. 4, 1996, to R. Shet, the disclosure of which is hereby incorporated herein in its entirety by reference.

Another method of preparing the cellulose fibers useful in the present invention is to heat treat the fibers, e.g., such as by way of example, as described in U.S. Pat. No. 5,834,095 issued Dec. 1, 1998 to J. Dutkiewicz et al.

Another method of preparing the cellulose fibers useful in the present invention is to treat the cellulose fibers with a basic solution to swell the cellulose fibers. The basic solution may be prepared using an alkali metal hydroxide material, such as sodium hydroxide. Any combination of treatment in a basic solution and time which is effective in preparing the fibers, without undesirable damage to the fibers, so that a first wicking layer prepared from the basic-treated fibers exhibits the preferred liquid transport properties described herein, is suitable for use in the present invention.

The cellulose fibers first are added to a basic solution, allowed to soak for a preferred amount of time, and then neutralized with an acid solution to a pH of about 7. The treated cellulosic fibers then are used to prepare an absorbent structure.

If sodium hydroxide is used to prepare the basic solution used to treat the cellulosic fibers, the basic solution has a concentration of from about 50 to about 500 grams of sodium hydroxide per liter of water and preferably from about 100 to about 300 grams of sodium hydroxide per liter of water. The treatment time of the cellulose fibers is from about 1 to about 10 minutes.

It also has been discovered that, by using a steam explosion process for treating cellulosic fibers and by using appropriate treatment conditions, modified cellulosic fibers exhibiting preferred properties are prepared by an efficient and effective process.

Other methods of preparing the cellulose fibers for use in a first wicking layer of the present invention include oxidizing the cellulose. In addition, cellulose fibers prepared from one of the above-described methods may be mixed together with non-treated cellulose fibers, with cellulose fibers prepared from another one of the above-described methods, or other non-cellulosic fibers to form a blend of fibers that is useful in preparing the first wicking layer of the present invention.

The detailed description of the multifunctional material of the present invention includes specific embodiments and applicable alternatives, ranges, and products for the structure and method of providing the multifunctional material of the present invention.

Actual examples of the multifunctional material (MAC) of the present invention were prepared with UnCreped Through Air Dried (UCTAD) basesheets serving as the interconnected capillary system (ICS) of the present invention and various superabsorbent material SAMs in the form of particulates or superabsorbent material SAM extenders. By CR designations is meant southern softwood kraft pulp made by Alliance Corporation. By HPZ designations is meant southern softwood kraft pulp made by Buckeye Cellulose Company. Favor SAP 870 is a superabsorbent material manufactured by Stockhausen, Inc. of Greensboro, N.C.

The UnCreped Through Air Dried sheets were high flux distribution materials as well as highly permeable UnCreped Through Air Dried sheets made with Bleached Chemi-Thermal Mechanical Pulp (BCTMP).

The following Example I produced a multifunctional material made by imparting superabsorbent material SAM particulates on UCTAD substrates.

EXAMPLE I

A multifunctional material was produced by pressing Super-Absorbent Material (SAM) of the type Favor 880 having a particle size distribution of 300–600 microns in between layers of Un-Creped Through Air Dried (UCTAD) tissue having a composition of 50:50 CR1654/HPZ and a basis weight of 67 gsm. A bottom layer of UCTAD was embossed to form depressions in the sheet. The preferred amount of SAM then was placed into the depressions in an amount of 150–175 gsm SAM. A second sheet of UCTAD was sprayed with a fine mist of water to achieve a moisture content of approximately 40% by weight. The wet layer of UCTAD then was placed on top of the UCTAD layer containing the SAM in the depressions. The structure then was pressed to form the bond between the two layers. The water was used to enhance bonding between the two sheets as hydro-bonding. The depressions containing the SAM protected the open areas in the UCTAD sheet from being pressed. The depressions protected the distribution material's ability to wick liquid. A MAC also was produced to contain an equivalent amount of SAM as compared to a diaper (>300 gsm). Two layers of SAM were pressed in between three layers of UCTAD.

The MACs produced using the method of Example I were very thin materials having high SAM content by weight (>50%). The materials of Example I were observed to have excellent intake, spreading, and capacity properties. The integrity of these MACs also was much better than the weak absorbent cores used in disposable absorbent products today.

The following Example II describes MACs for spreading and liquid retention ability.

EXAMPLE II

MACs were produced by imprinting SAM between layers of UCTAD, barrier tissue, and combinations of both. The process by which these materials were manufactured was produced by spreading SAM onto a bottom sheet of tissue. The bottom layer containing the SAM then was sprayed with a fine water mist. A top sheet of tissue was laid on the bottom layer, and the laminate was pressed to bond the two layers of tissue together forming a sandwich. These sandwiches were very thin and flexible. Combinations of these MACs included the following structures.

(1) UCTAD(67 gsm)-SAM(120 gsm)-UCTAD(67 gsm). Total weight was 254 gsm.
(2) UCTAD(67 gsm)-SAM(120 gsm)-Barrier tissue(20 gsm) Total weight was 207 gsm. By barrier tissue is meant pulp sheet of 20 gsm basis weight.
(3) Barrier tissue(20 gsm)-SAM(86 gsm)-Barrier tissue (20 gsm) Total weight was 126 gsm.

These MACs produced in Example II were found to be materials which transport and retain the liquid in the sample. The MAC using two layers of barrier tissue did not show any spreading qualities when wetted. A commercial Gel-Lok (tissue/SAM/tissue sandwich composite) performed relatively poorly as well. The UCTAD was observed to be necessary in these MACs to spread the liquid in the sample more quickly so the SAM can lock it away. The materials containing UCTAD showed excellent transporting and retention qualities even though they will not vertically wick liquid as well as the MACs described above as structures (1), (2), and (3).

The following Examples III–IV describe MACs made by combining UCTAD substrated into layers with SAM extenders.

EXAMPLE III

As control, three layers of 67 gsm UCTAD (50/50 CR1654/HPZ) were produced.

| Time to | Pickup Rate (× $10^{-4}$ g/min * gsm * inch) | Total Fluid (g) |
|---|---|---|
| 10 cm, 28 sec | 113 | |
| 15 cm, 1.7 min | 37 | app. 8 |

EXAMPLE IV

A mixture of curled CR55/Favor 870 was made into absorbent composition.

Three layers of 67 gsm UCTAD (50/50 CR54/HPZ), with 2.1 g absorbent composition were placed between two of the layers.

| Time to | Pickup Rate (× $10^{-4}$ g/min * gsm * inch) | Total Fluid (g) |
|---|---|---|
| 10 cm, 1.7 min | 49.5 | 8 |
| 15 cm, 15.5 min | 15 | 25 |

EXAMPLE V

A mixture of 80/20 Rayon/Favor 870 was made into an absorbent composition.

Three layers of 67 gsm UCTAD (50/50 CR54/HPZ), with 2.1 g absorbent composition were placed between two of the layers.

| Time to | Pickup Rate (× $10^{-4}$ g/min * gsm * inch) | Total Fluid (g) |
|---|---|---|
| 10 cm, 1.7 min | 47 | 9 |
| 15 cm, 24 min | 11 | 30 |

The following Examples VI–IX produced MACs with SAM particles embedded in tissue. In one series of experiments, the tissue was UCTAD web. It was possible to retain up to 45% of SAM in the web. Most of the SAM particulates were located on one side of the web so that the other side was substantially free of SAM to take advantage of liquid intake and transport functions of the interconnected capillary system created by the fiber network ICS of the present invention. The obtained materials were observed to be thin, flexible, and exhibited surprisingly strong attachment of SAP to the fibrous web. The MACs obtained this way were observed to have excellent liquid transport, i.e., intake, spreading, and wicking properties, because of high permeability, porosity, and stable capillarity. They were able to retain large amounts of liquid without run-off. Additional surprising effects were appearance, thinness, flexibility, and integrity of the material as a whole. No SAM was observed to be falling off. The MACs looked and felt the same as the UCTAD substrates without SAM.

In all the following Examples VI–IX, the lab-sized apparatus was used to fabricate MAC. The superabsorbent additive was "fines" Favor 870. The lab-sized device functioned as follows: The cellulose material was unwound onto a 25 cm wide wire conveyor moving at 244 cm/min. The conveyor belt traveled over a top of the vacuum box. The vacuum box was under negative pressure of approximately 500 pascals.

The particulate material was metered from a 15 cm wide vibrational feeder at 171 g/min onto the top of the cellulose material. The contact point of the particulate material with the cellulose material fell, where a 49 mm long slot was present in the vacuum box under the wire. The vacuum aided in the transfer and retention of the particulate material within the cellulose material.

Short samples of material were made. The excess of particulate material was shaken off of the cellulose material, and the retention of the particulate material was measured gravitationally.

Microscopic observations were conducted of the superabsorbent distribution in z-direction of the sheet. There was a gradient in the particle distribution throughout the thickness of the base material. One side of the material was essentially free of the SAM particles.

EXAMPLE VI

The base material was (50/50 CR1654/HPZ) UCTAD of 67 gsm basis weight.

SAM Particle

| size ($\mu$m) | BW, (gsm) | SAM |
|---|---|---|
| No SAP | 19.79 | 0 |
| 90–150 $\mu$m | 20.02 | 1.18% |
| 75–90 $\mu$m | 20.19 | 2.01% |
| 75–90 $\mu$m | 20.24 | 2.23% |
| 53–75 $\mu$m | 20.33 | 5.01% |
| 38–53 $\mu$m | 22.28 | 11.20% |
| 38–53 $\mu$m | 22.63 | 12.58% |

EXAMPLE VII

The base material was 50/50 CR1654/HPZ UCTAD. The 13.3% retention of superabsorbent was obtained.

EXAMPLE VIII

The UCTAD made with mercerized LL-19 was used.

| Basis Weight, gsm | % SAM |
|---|---|
| 48.6 | 21–30 |
| 92.2 | 9–13 |
| 218.7 | 7–8 |

EXAMPLE IX

| Description | BW, gsm | % SAM |
|---|---|---|
| BCTMP UCTAD 33 gsm | | |
| 2 No SAM, 960518 | 20.01 | 0 |
| 3 ALL SIZES | 27.66 | 27.67% |
| 4 ALL SIZES | 30.78 | 35.01% |
| 5 ALL SIZES | 28.20 | 29.05% |
| 7 960528 all sizes | 30.17 | 33.69% |
| BCTMP, UCTAD 33 gsm | | |
| 10 No SAM | 35.00 | 0 |
| 11 960611 all sizes | 56.73 | 38.29% |
| 12 60612 all sizes | 55.46 | 36.88% |
| 13 60612 all sizes | 50.48 | 30.66% |
| 15 12 <38–53 | 52.37 | 33.16% |
| 16 12 <38–53 | 51.98 | 32.66% |
| BCTMP, UCTAD 40 gsm | | |
| 20 No SAM | 40.95 | 0 |
| 21 960611 all sizes | 56.62 | 27.68% |
| 22 960619 all sizes | 75.13 | 45.50% |

By applying the SAM to various BCTMP materials, the retention of SAM from 27 to 45% was achieved.

EXAMPLE X

An UCTAD/Adhesive/Favor 880/Adhesive/UCTAD Material was prepared and identified as Sample BK-1 and Sample BK-2. Composites BK-1 and BK-2 were layered composites having a structure of UCTAD/Adhesive/Favor 880/Adhesive/UCTAD.

Figure 2:
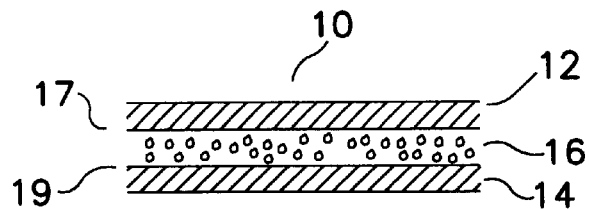
FIG. 2 shows a schematic cross sectional configuration of a composite absorbent structure in accordance with the present invention.

Referring now to FIG. 2, the cross sectional configuration of Samples BK-1 and BK-2 is shown. A composite 10 has a first UCTAD layer 12 and a second UCTAD layer 14 on opposite sides a superabsorbent layer 16. Adhesive layers 17 and 19 secure the composite together.

The difference in the two composite samples BK-1 and BK-2 was only the type of adhesive used.

The process of making such structures included five steps. (1) spread five grams per square meter of adhesive material is spread onto an UCTAD sheet; (2) formed a 160 gram per square meter uniform layer of particulate of Favor 880 on the top of the Adhesive/UCTAD sheet; (3) spread another 5 grams per square meter of adhesive material onto Favor 880/Adhesive/UCTAD; (4) covered an UCTAD sheet on the top Adhesive/Favor 880/Adhesive/UCTAD sheet; and (5) pressed the sheet by a nip roller at 40 pounds per linear inch.

The UCTAD tissue used in Example X had a basis weight of about 67 GSM and a density of about 0.10 grams per cubic centimeter. This UCTAD tissue also had a vertical wicking flux of 0.0029 grams of fluid per gram of dry material per square meter per inch width per minute. This UCTAD sheet also was micro-strained at 0.015 inches of depth using the microstaining process described in U.S. Pat. No. 5,743,999.

The SAM used in Example X was a commercial polyacrylate superabsorbent designated as Favor 880 obtained from Stockhausen. The superabsorbent had a degree of neutralization of about 70 mole percentage. Favor 880 had a particle size range from 150 to 850 microns for this Example X.

The adhesive used in Example X included two types of adhesive material. In BK-1, the adhesive designated as H2525A was obtained from the Ato-Findley (Varde, Denmark). In BK-2, the adhesive designated as NS5610 was obtained from National Starch Company.

Absorbent Capacity vertical wicking tests were carried out, and the results are shown in Table 1.

posite. The Kymene spray was used to crosslink the polyacrylic acid which bonds the cellulose and superabsorbent particles to the BCW and UCTAD layers to form the absorbent composite.

An absorbent composite Sample BK-4 was prepared using the same equipment setup as described for Sample BK-3. The following changes in composition were made for Sample BK-4 compared to Sample BK-3. The cellulose fluff used in Sample BK-4 was 188 gsm. The polyacrylic acid in the solution sprayed had a degree of neutralization of 20% sodium polyacrylate and also contained 2% by weight of ammonium zirconium carbonate. Kymene solution was not sprayed while making the composite.

TABLE 1

| Sample | Liquid in Comp. (g/g) Ave.; | St. Dev. | Saturation of Comp. (%) | Liquid in SAP (g/g) Ave.; | St. Dev. | Liquid in UCTAD (g/g) Ave.; | St. Dev. |
|---|---|---|---|---|---|---|---|
| BK-1 | 8.5 | 0.8 | 44.3 | 12.1 | 0.4 | 4.7 | 1.1 |
| BK-2 | 6.3 | 0.5 | 32.8 | 10.1 | 0.7 | 3.8 | 0.2 |

EXAMPLE XI

An absorbent composite sample BK-3 was prepared using an air-forming process with the capability to unwind materials from a roll and also spray additives to form the absorbent composite.

Figure 3:
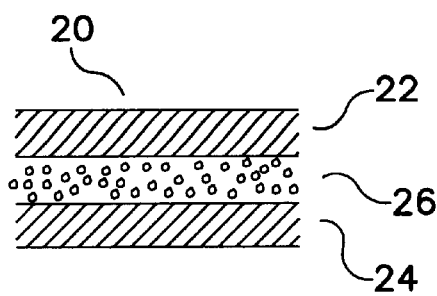
FIG. 3 shows a schematic cross sectional configuration of a composite absorbent structure in accordance with the present invention.

A 80 gsm bonded carded web (BCW) made of polyethylene/polyester bicomponent fiber was unwound from a roll onto a forming wire equipped with vacuum to enable other materials to added. 258 gsm of cellulose fluff and 189 gsm of polyacrylate superabsorbent were delivered through a nozzle located about 10 inches above the forming wire at a velocity of about 150 ft/sec. using air to transport the mixture. About 80 gsm of polyacrylic acid solution (15 % solids content) was added through two atomizing nozzles located between the fluff/SAM nozzle and the forming wire. About 20 gsm of crosslinking agent Kymene 557 LX (6.0% solids content) also was added through two atomizing nozzles located between the fluff/SAM nozzle and the forming wire. The polyacrylic acid and Kymene spray nozzles were positioned to obtain a uniform coating of polyacrylic acid and Kymene on the cellulose fluff / superabsorbent particulates being added. Finally, a 70 gsm uncreped through-air dried (UCTAD) cellulose sheet was unwound from a roll and layered onto the air-formed com- Referring now to FIG. 3, the cross sectional configuration of Samples BK-3 and BK-4 is shown. A composite 20 has a surge layer 22 and a UCTAD layer 24 on opposite sides a super-absorbent/fluff layer 26.

Absorbent Capacity vertical wicking tests were carried out, and the results are shown in Table 2.

TABLE 2

| Sample | Liquid in Comp. (g/g) Ave.; | St. Dev. | Saturation of Comp. (%) | Liquid in SAP (g/g) Ave.; | St. Dev. | Liquid in UCTAD (g/g) Ave.; | St. Dev. |
|---|---|---|---|---|---|---|---|
| BK-3 | 0.17 | 0.09 | 1.3 | 0.35 | 0.02 | 1.4 | 0.4 |
| BK-4 | 0.76 | 0.30 | 5.7 | 0.45 | 0.17 | 2.1 | 0.4 |

EXAMPLE XII

An UCTAD/Danaklon/Favor 880/Danaklon/UCTAD Material was prepared and identified as Samples BK-7, BK-8, BK-9, BK-10, and BK-11. Composites BK-7, BK-8, BK-9, BK-10, and BK-11 were air-laid composites having a structure of UCTAD/Danaklon/Favor 880/Danaklon/ UCTAD.

Figure 4:
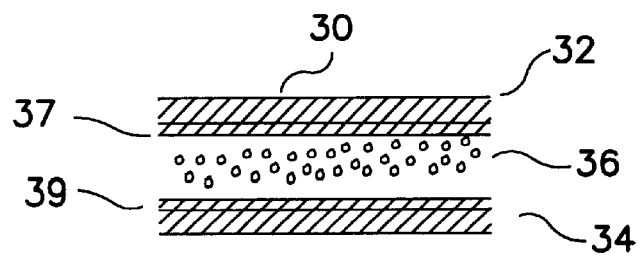
FIG. 4 shows a schematic cross sectional configuration of a composite absorbent structure in accordance with the present invention.

Referring now to FIG. 4, the cross sectional configuration of Samples BK-7, BK-8, BK-9, BK-10, and BK-11 is shown. A composite 30 has a first UCTAD layer 32 and a second UCTAD layer 34 on opposite sides of a superabsorbent layer 36. Danaklon layers 37 and 39 secure are positioned between the UCTAD layers and the superabsorbent.

The process of making the structures for Samples BK-7, BK-8, BK-9, BK-10, and BK-11 included five steps: (1) formed an air laid Danaklon layer having a basis weight of Danaklon ranging from 0 to 80 grams per square meter on top of a UCTAD sheet; (2) formed a 150 gram per square meter uniform layer of particulate of Favor 880 on the top of the Danaklon/UCTAD sheet; (3) formed another air laid Danaklon layer having a basis weight of Danaklon ranging from 0 to 80 grams per square meter on top of the Favor 880/Danaklon/UCTAD sheet; (4) covered an UCTAD sheet on the top; and (5) pressed the composite by a Carver laboratory press (Model 2333) at a temperature of 150° C. under 15,000 psi for 30 seconds.

In the case of Example BK-0, no Danaklon staple fiber was used in that composite, and about 10 grams per square meter of adhesive material was spread onto the UCTAD and replaced Danaklon staple fiber. The BK-0 composite was pressed at room temperature under 15,000 psi for 10 seconds.

The UCTAD tissue used in Example XII had a basis weight of about 67 gsm and a density of about 0.10 grams per cubic centimeter. This UCTAD tissue also had a vertical wicking flux of 0.0029 grams of fluid per gram of dry material per square meter per inch width per minute. This UCTAD sheet also was micro-strained at 0.015 inches of depth.

The Danaklon used in Example XII was a commercial sheath/core polyethylene/polypropylene fiber having a diameter of 2.2 denier and a length of 6 mm manufactured by the Danaklon A/S Company.

The SAM used in Example XII was a commercial polyacrylate superabsorbent designated as Favor 880 obtained from Stockhausen. The superabsorbent had a degree of neutralization of about 70 mole percentage. Favor 880 had a particle size range from 150 to 850 microns for this Example XII.

Absorbent Capacity vertical wicking tests were carried out, and the results are shown in Table 3.

TABLE 3

| Sample | Liquid in Comp. (g/g) | | Saturation of Comp. (%) | Liquid in SAP (g/g) | | Liquid in UCTAD (g/g) | |
|---|---|---|---|---|---|---|---|
| | Ave.; | St. Dev. | | Ave.; | St. Dev. | Ave.; | St. Dev. |
| BK-0 | 7.3 | 0.6 | 42.9 | | | | |
| BK-7 | 5.4 | 0.5 | 31.8 | 8.4 | 0.9 | 2.2 | 0.9 |
| BK-8 | 3.5 | 0.7 | 20.6 | 4.7 | 1.3 | 2.3 | 0.3 |
| BK-9 | 2.9 | 0.5 | 17.0 | 2.9 | 0.7 | 2.9 | 0.4 |
| BK-10 | 1.4 | 0.3 | 8.2 | 1.0 | 0.94 | 2.0 | 0.1 |
| BK-11 | 0.8 | 0.1 | 0.5 | 8.4 | 0.04 | 1.6 | 0.2 |

EXAMPLE XIII

Composites Sample BK-30 and Sample BK-31 were single UCTAD tissues having SAM embedded in the tissue through an air laying process. The process of making such structures includes forming a superabsorbent uniform layer of particulate on an UCTAD sheet. While the air-laying of SAM is taking place a vacuum is applied on the opposite side of the sheet causing SAM particles to embed themselves into the UCTAD tissue.

Figure 5:
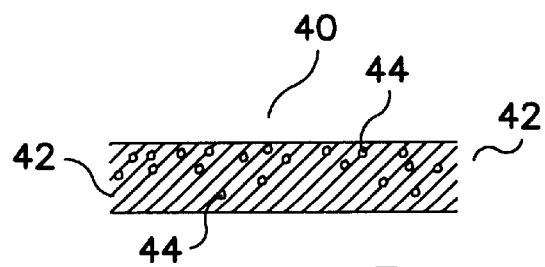
FIG. 5 shows a schematic cross sectional configuration of a composite absorbent structure in accordance with the present invention.

Referring now to FIG. 5, the cross sectional configuration of Samples BK-30 and BK-31 is shown. A composite 40 has an UCTAD tissue sheet 42 embedded with superabsorbent particles 44.

The UCTAD tissue used in Example XIII had a basis weight of about 67 GSM and a density of about 0.10 grams per cubic centimeter. This UCTAD tissue also had a vertical wicking flux of 0.0029 grams of fluid per gram of dry material per square meter per inch width per minute. This UCTAD sheet also was micro-strained at 0.015 inches of depth.

The SAM used in Example XIII was a commercial polyacrylate superabsorbent designated as Favor 880 obtained from Stockhausen. The superabsorbent had a degree of neutralization of about 70 mole percentage. Favor 880 had a particle size range from 0 to 250 microns for this Example XIII.

Absorbent Capacity vertical wicking tests were carried out, and the results are shown in Table 4.

TABLE 4

| Sample | Liquid in Comp. (g/g) | | Saturation of Comp. (%) |
|---|---|---|---|
| | Ave.; | St. Dev. | |
| BK-30 | 4.7 | 1.2 | 63.5 |
| BK-31 | 5.2 | 0.3 | 49.5 |

EXAMPLE XIV

Samples of UCTAD / SAM / UCTAD composites were submitted for determination of the Contact Intimacy as per the Contact Intimacy analysis method described herein above.

Figure 6:
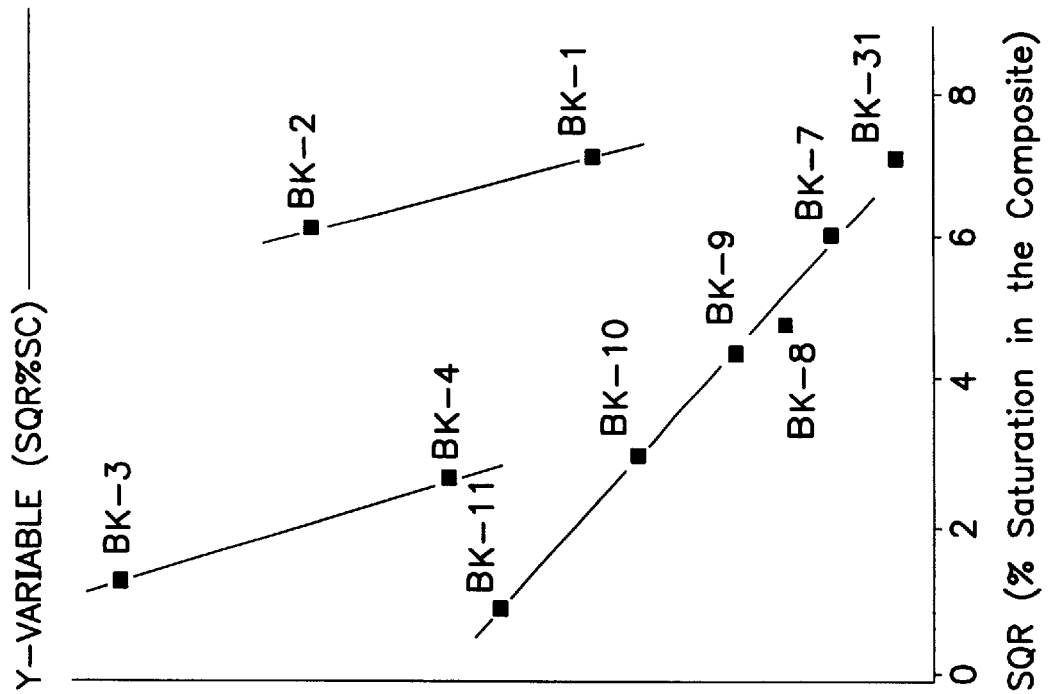
FIG. 6 shows a graphical depiction of Contact Intimacy results for composite absorbent structures in accordance with the present invention.

Image analysis was performed on a cross-section of the samples from Examples X, XI, XII, and XIII with the routine, "CONIM7", with Layers set to 2. FIG. 6 shows a graphical depiction of the results.

In one embodiment of the present invention, a disposable absorbent product is provided, which disposable absorbent product includes a liquid-permeable topsheet, a backsheet attached to the topsheet, and an absorbent structure positioned between the topsheet and the backsheet wherein the absorbent structure is a composite absorbent structure as described herein.

One embodiment of the invention will be described in terms of the use of an absorbent structure in an infant diaper. It is to be understood that the absorbent structure is equally suited for use in other disposable absorbent products known to those skilled in the art such as training pants, feminine care products such as pads and tampons, incontinence products, and health care products such as capes or gowns.

Exemplary materials suitable for use as the topsheet are liquid-permeable materials, such as spunbonded polypropylene or polyethylene having a basis weight of from about 15 to about 25 grams per square meter. Exemplary materials suitable for use as the backsheet are liquid-impervious materials, such as polyolefin films, as well as vapor-pervious materials, such as microporous polyolefin films.

Disposable absorbent products, according to all aspects of the present invention, are subjected during use to multiple insults of a body liquid. Accordingly, the disposable absorbent products are capable of absorbing multiple insults of body liquids in quantities to which the absorbent products and structures will be exposed during use. The insults are separated from one another by a period of time.

Test Method—Wet Curl of Fibers

The Wet Curl value for fibers was determined by using an instrument which rapidly, accurately, and automatically determines the quality of fibers, the instrument being available from OpTest Equipment Inc., Hawkesbury, Ontario, Canada, under the designation Fiber Quality Analyzer, OpTest Product Code DA93.

A sample of fibers was obtained from the fiber pulp used to prepare the sample handsheet. The fiber sample was poured into a 600 milliliter plastic sample beaker to be used in the Fiber Quality Analyzer. The fiber sample in the beaker was diluted with tap water until the fiber concentration in the beaker was about 10 to about 25 fibers per second for evaluation by the Fiber Quality Analyzer.

An empty plastic sample beaker was filled with tap water and placed in the Fiber Quality Analyzer test chamber. The <System Check> button of the Fiber Quality Analyzer was then pushed. If the plastic sample beaker filled with tap water was properly placed in the test chamber, the <OK> button of the Fiber Quality Analyzer was then pushed. The Fiber Quality Analyzer then performs a self-test. If a warning was not displayed on the screen after the self-test, the machine was ready to test the fiber sample.

The plastic sample beaker filled with tap water was removed from the test chamber and replaced with the fiber sample beaker. The <Measure> button of the Fiber Quality Analyzer was then pushed. The <New Measurement> button of the Fiber Quality Analyzer was then pushed. An identification of the fiber sample was then typed into the Fiber Quality Analyzer. The <OK> button of the Fiber Quality Analyzer was then pushed. The <Options> button of the Fiber Quality Analyzer was then pushed. The fiber count was set at 4,000. The parameters of scaling of a graph to be printed out may be set automatically or to preferred values. The <Previous> button of the Fiber Quality Analyzer was then pushed. The <Start> button of the Fiber Quality Analyzer was then pushed. If the fiber sample beaker was properly placed in the test chamber, the <OK>button of the Fiber Quality Analyzer was then pushed. The Fiber Quality Analyzer then began testing and displayed the fibers passing through the flow cell. The Fiber Quality Analyzer also displayed the fiber frequency passing through the flow cell, which should be about 10 to about 25 fibers per second. If the fiber frequency is outside of this range, the <Stop>button of the Fiber Quality Analyzer should be pushed and the fiber sample should be diluted or have more fibers added to bring the fiber frequency within the preferred range. If the fiber frequency is sufficient, the Fiber Quality Analyzer tests the fiber sample until it has reached a count of 4000 fibers at which time the Fiber Quality Analyzer automatically stops. The <Results> button of the Fiber Quality Analyzer was then pushed. The Fiber Quality Analyzer calculates the Wet Curl value of the fiber sample, which prints out by pushing the <Done> button of the Fiber Quality Analyzer.

Test Method—Water Retention Value

A 0.5 gram cellulosic fiber sample was obtained and dispersed into about 200 grams of deionized water using a Hobart Company Model N 50 blender set on the low speed setting for about 30 seconds. The cellulosic fiber/water suspension was transferred to a beaker and allowed to sit for about 16 hours. The supernate water was decanted and the cellulosic fibers were placed into a centrifuge (Dynac II by Clay Adams, Division of Becton Dickinson & Co., Model 5025, serial 012, cat. No. 0103) tube fitted with a screen. The cellulosic fibers then were centrifuged under a force of about 1000 times gravity for about 20 minutes. The cellulosic fibers then were removed from the centrifuge tube and weighed (giving a wet weight $W_w$). The cellulosic fibers were then dried at about 105° C. for about 120 minutes. The cellulosic fibers were then reweighed (giving a dry weight $W_D$). The Water Retention value then was calculated by subtracting the dry weight ($W_D$) from the wet weight ($W_w$) and then dividing that value by the dry weight ($W_D$). The Water Retention value were reported as the grams of water retained per gram of dry cellulosic fibers.

Preparation of Wet-Laid Handsheet

A 43 cm by 43 cm standard handsheet having a basis weight of about 200 grams per square meter was prepared using a preferred fiber sample by using a 41 cm by 41 cm cast bronze wet-laid hand-sheet former mold, available from Voith Corporation.

A British Disintegrator mixer, available from Testing Machines, Inc., was filled with about 2 liters of distilled water at room temperature (about 230° C.) and about 37.3 grams of the fiber sample. The counter on the British Disintegrator was set to zero and the cover was placed on the British Disintegrator. The British Disintegrator was turned on until the counter runs to about 600. Alternatively, the British Disintegrator may be run for about 5 minutes. A bucket was filled with about 8 liters of distilled water. The contents of the British Disintegrator was then also poured into the bucket.

The handsheet former, having a chamber about 30 cm deep, was filled partially with tap water to a depth of about 13 cm. The contents of the bucket were then poured into the handsheet former chamber. A dedicated stirrer then was used to mix the suspension in the handsheet former chamber. The stirrer was moved slowly up and down 6 times to cause small vortexes, but to avoid causing large vortexes, in the square pattern of the handsheet former. The stirrer was then removed and the suspension was drained through the forming screen of the handsheet former. The handsheet former was then opened and two layers of blotting paper were placed on the top of the handsheet. A roller, having the equivalent of about 3.9 N/cm, was moved back and forth once on each of the left side, the right side, and the center of the formed handsheet. The blotting paper, with the formed handsheet attached, was then lifted off the forming screen. The blotting paper was then placed on a table such that the formed handsheet faced up-wards. An 46 cm by 46 cm, 4 mesh steel screen was placed on top of the handsheet. The blotting paper, handsheet, and screen were then flipped so that the screen was on the bottom and the blotting paper was on top. The blotting paper was then peeled off of the handsheet, leaving the handsheet on the screen. The edges of the handsheet were fastened to the screen using binder clips. The handsheet was left overnight to air-dry. The handsheet, attached to the screen, was then placed in an oven and dried at about 105° C. for about 60 minutes. The handsheet then was removed from the oven and removed from the screen. The sheet then was equilibrated in a TAPPI conditioned room for 60 minutes. The sheet then was ready for evaluation for liquid distribution properties.

Test Method—Thickness and Dry Density of an Absorbent Structure

From a handsheet prepared according to the procedure described herein, a strip of sample handsheet material having a width of about 5 cm and a length of about 38 cm was obtained by using a textile saw available, for example from Eastman, Machine Corp., Buffalo, N.Y. The sample strip was cut at least about 2.5 cm away from the edge of the handsheet so as to avoid edge effects. The sample strip was marked in about 10 millimeter intervals using water-soluble ink.

To measure the bulk, i.e, thickness, of the sample strip, a bulk meter accurate to at least about 0.01 millimeter, such as a bulk meter available from Mitutoyo Corporation, was used. A platen of about 2.54 cm diameter platen was used to measure the thickness, with the platen being parallel to the base of the thickness meter. The platen imposed 340 Pa pressure on the material of a sample strip. The thickness of the sample strip was measured in about 50 millimeter intervals along the length of the sample strip and then averaged. The average thickness of the sample strip was then used to calculate the dry density of the sample strip, using the weight and dimensions of the sample strip. The wet density of the sample strip may be determined by ASTM D5729-95, which is hereby incorporated by reference as if set forth herein ver batim, after the sample strip has evaluated for Liquid Flux values.

Test Method—Vertical Wicking Absorbent Capacity

The objective of this test was to quantify the ability of a given absorbent material a) to wick saline to relatively high height (13–17 cm) and b) to retain the liquid at the height between the 13th and 17th cm.

The performance of UCTAD/SAP composite structures were quantified by efficiency in moving liquid up against gravity and transferring it from the UCTAD tissue to the retention component.

Various techniques can be used to measure the amount of saline contained in the absorbent material after wicking such as gravimetrical analysis (liquid balance before and after the wicking) or X-ray densitometry. Although the latter method is reliable and convenient, it requires the use of custom made equipment. The former approach may be replicated by one skilled in the art.

Figure 7:
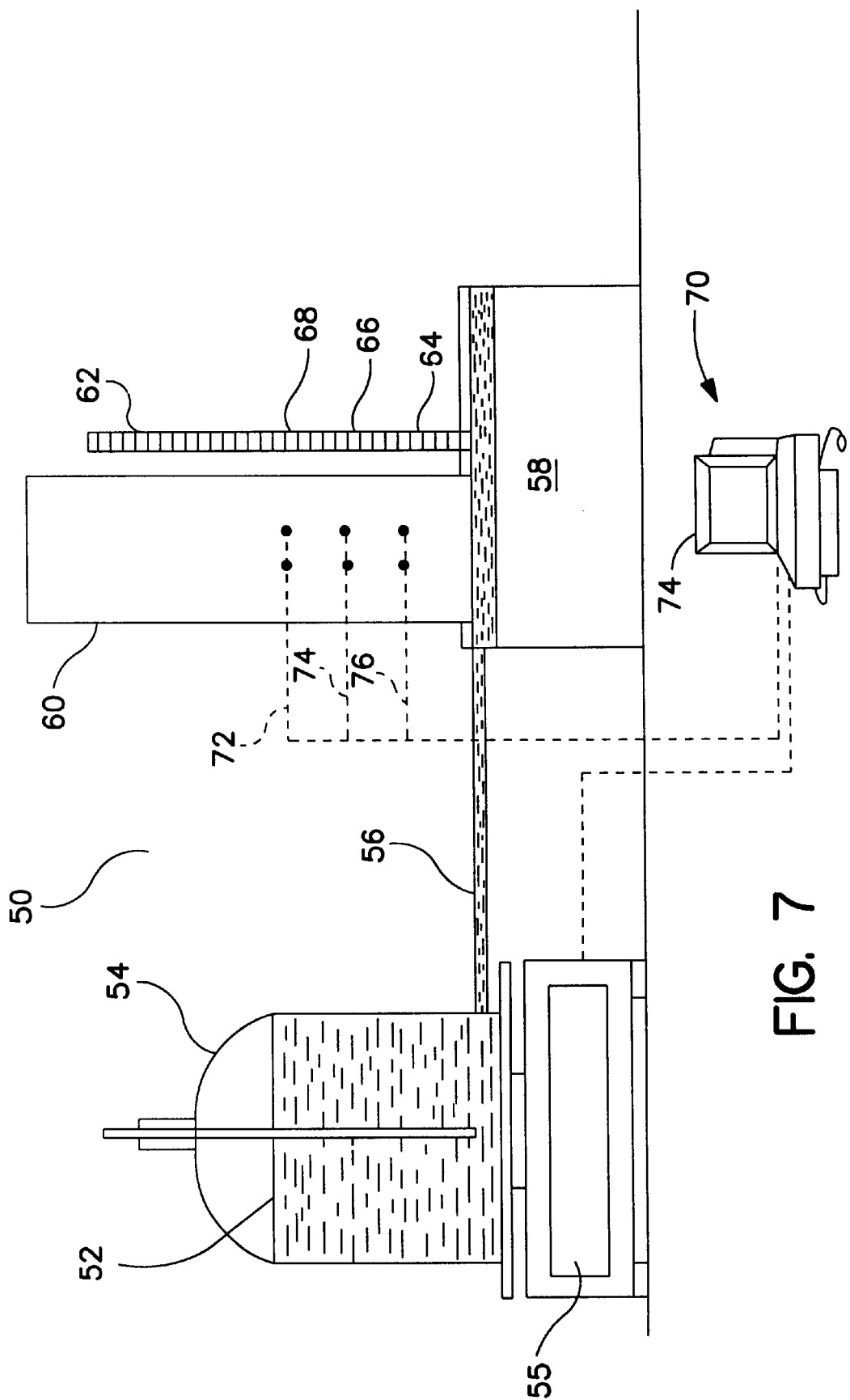
FIG. 7 shows a schematic of a wicking test apparatus used in accordance with the present invention.

In this method, a 23 cm by 5 cm sample is cut out from an absorbent material, for example, from a laminate structure made with distribution tissue and retention component (SAP, SAP and fluff mixture, SAP fibrous nonwoven). The sample is weighed to calculate the weight of its 4 cm length and placed in the Vertical Wicking Apparatus as shown in FIG. 7. The wicking time was established at 30 min. to allow for equilibration of the tested material. After 30 min., the upper segment of the tested sample (between the 13th and the 17th cm) was cut out and weighed.

To calculate the Absorbent Capacity (in g of liquid per g of dry material) at the 13–17 cm height, the above upper part was dried (22 hours, 105° C.) and wet weight was compared with the weight after drying. The dry weight of the 4 cm segment was calculated from the weight recorded before the wicking experiment and compared with the wet weight.

When the dry weight of the 4 cm segment was calculated from the weight recorded before the wicking experiment and compared with the wet weight, additional analysis of the sample may be analyzed after wicking. The partition of the liquid was quantified between the UCTAD material and the retention layer by separating these two components and then recording wet weights and the weights after drying (22 hours, 105° C.).

The vertical distances from surface of the solution to the liquid front traveling up the sample strip and the liquid weight absorbed by the sample strip were recorded at various times. Not more than 30 seconds should elapse between successive height, weight, and time recordings. Depending on how quickly the liquid front travels up the sample strip, it may be appropriate to record measurements more frequently.

Test Method—Vertical Liquid Flux

The Vertical Liquid Flux test is based on the procedure as set forth in U.S. Pat. No. 5,843,852 which is hereby incorporated by reference and included herein as if set forth verbatim.

Referring now to FIG. 7, a wicking test apparatus 50 is shown having a reservoir of liquid 52 in aspirator bottle 54 positioned on a balance 55. Liquid feed is passed in line 56 to liquid distributor 58. Sample 60 is placed by ruler 62 having graduated mark 64 at a distance of 5 cm up the ruler 62, graduated mark 66 at a distance of 10 cm up the ruler 62, and graduated mark 68 at a distance of 15 cm up the ruler 62. An automated apparatus 70 having electrode feeds 72, 74, and 76 to computer 74 may be substituted for the manual visual measurements, and accuracy and precision of measurements may be enhanced relative to manual visual measurements.

A plot of the liquid front height versus time was used to determine the Wicking Time to about 5 centimeters and to about 15 centimeters. The weight of the liquid absorbed by the sample strip was plotted versus time. The Vertical Liquid Flux value of the sample strip at a particular height was the slope of the weight versus time plot at that height, in grams per centimeters, times the length of the sample strip in centimeters divided by the mass of the sample strip in grams, as shown in Equation 2.

$$\text{Vertical Liquid Flux} = \frac{(Me - Md) \times Ls}{(Te - Td) \times Ms} \qquad \text{Eq. 2}$$

where:

Te represents recorded time e, in seconds; Td represents recorded time d, in seconds;

Me represents weight measured at time e, in grams;

Md represents weight measured at time d, in grams;

Ls represents the length of the dry sample strip prior to testing, including the portion of the strip that is- submerged in the test solution during testing, in centimeters; and Ms represents the mass of the dry sample strip prior to testing, in grams.

The terms "d" and "e" represent successive times at which height and weight were measured in the series of measurements a, b, . . . , d, e, . . . ,z. The time required for the liquid front to reach 5 or 15 centimeters was between d seconds and e seconds. When determining the slope of the weight versus time plot for the purpose of calculating the Vertical Liquid Flux, it is preferred to use more than two weight and time values near the desired height. Various graphical and statistical techniques confirm accuracy of the estimate of Vertical Liquid Flux at either 5 or 15 centimeters.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A composite absorbent structure, comprising:
   a. a first wicking layer comprising wettable fibers, wherein the first wicking layer exhibits a vertical liquid flux rate value at a height of about 15 centimeters of at least about 0.08 grams of liquid per minute per gram of absorbent structure per meter length of the first wicking layer;

b. a second retention layer comprising a hydrogel-forming polymeric material; and c. a bonding agent for bonding said first wicking layer and said second retention layer to form a composite absorbent structure having a minimum contact intimacy ratio for providing a liquid transport function and a liquid retention function such that the first wicking layer and the second retention layer are combined together in a manner to obtain a contact to achieve liquid transport and liquid retention functions at a length of at least about 15 centimeters, a saturated capacity of at least about 5 grams of liquid per gram of composite absorbent structure, and an Absorbent Capacity at 15 cm of at least about 5 grams of liquid per gram of second retention layer.

2. The composite absorbent structure of claim 1, wherein said first wicking layer comprises wettable cellulosic fibers.

3. The absorbent structure of claim 2, wherein said bonding agent comprises Danaklon fibers.

4. The absorbent structure of claim 2, wherein said bonding agent comprises a hydrophilic hot melt adhesive.

5. The absorbent structure of claim 2, wherein said hydrogel-forming polymeric material comprises a superabsorbent.

6. The absorbent structure of claim 2, wherein said wettable cellulosic fibers exhibit a wet curl value between about 0.15 to about 0.20.

7. The absorbent structure of claim 2, wherein said first wicking layer exhibits a vertical liquid flux rate value at a height of about 15 centimeters of at least about 0.1 grams of liquid per minute per gram of first wicking layer per meter length of cross-sectional width of said first wicking layer.

8. The absorbent structure of claim 2, wherein said bonding agent comprises a sheath/core polyethylene/polypropylene fibers.

9. The absorbent structure of claim 2, wherein said bonding agent comprises a polyaminoamide epichlorohydrin wet strength resin.

10. The absorbent structure of claim 2, wherein said first wicking layer exhibits a vertical liquid flux rate value at a height of about 15 centimeters of at least about 0.2 grams of liquid per minute per gram of first wicking layer per meter length of cross-sectional width of said first wicking layer.

11. The absorbent structure of claim 2, wherein said first wicking layer exhibits a vertical liquid flux rate value at a height of about 5 centimeters of at least about 0.4 grams of liquid per minute per gram of first wicking layer per meter length of cross-sectional width of said first wicking layer.

12. The absorbent structure of claim 2, wherein said first wicking layer exhibits a vertical liquid flux rate value at a height of about 5 centimeters of at least about 0.6 grams of liquid per minute per gram of first wicking layer per meter length of cross-sectional width of said first wicking layer.

13. The absorbent structure of claim 2, wherein said wettable cellulosic fibers exhibit a wet curl value between about 0.11 to about 0.25, said first wicking layer exhibits a vertical liquid flux rate value at a height of about 5 centimeters of at least about 0.4 grams of liquid per minute, said first wicking layer exhibits a wicking time value of less than about 3.5 minutes, and said first wicking layer, having a basis weight of about 200 grams per square meter, exhibits a dry tensile strength at least about 2000 n/m of force per inch of first wicking layer width and a wet tensile strength at least about 200 n/m of force of first wicking layer width, wherein said fibers are present in said first wicking layer in an amount of from about 50 to about 100 weight percent, based on said total weight of said absorbent structure, and said first wicking layer exhibits a density between about 0.08 to about 0.5 grams per cubic centimeter.

14. A method of forming a composite absorbent structure, comprising:

a. providing a first wicking layer of wettable cellulosic fibers, wherein the first wicking layer exhibits a vertical liquid flux rate value at a height of about 15 centimeters of at least about 0.08 grams of liquid per minute per gram of absorbent structure per meter length of the first wicking layer;

b. providing a second retention layer of a hydrogel-forming polymeric superabsorbent material;

c. providing a bonding agent for bonding said first wicking layer and said second retention layer; and d. combining said first wicking layer, said second retention layer, and said bonding agent to form a composite absorbent structure having a minimum contact intimacy ratio for providing a liquid transport function and a liquid retention function such that the first wicking layer and the second retention layer are combined together in a manner to obtain a contact to achieve liquid transport and liquid retention functions at a length of at least about 15 centimeters, a saturated capacity of at least about 5 grams of liquid per gram of composite absorbent structure, and an Absorbent Capacity at 15 cm of at least about 5 grams of liquid per gram of second retention layer.

15. The method of forming a composite absorbent structure as set forth in claim 14, comprising providing a bonding agent of a sheath/core polyethylene/polypropylene fibers.

16. The method of forming a composite absorbent structure as set forth in claim 14, comprising providing a bonding agent of Danaklon sheath/core polyethylene/polypropylene fibers.

17. The method of forming a composite absorbent structure as set forth in claim 14, comprising providing a bonding agent of a polyaminoamide epichlorohydrin wet strength resin.

18. A disposable absorbent product comprising a liquid-permeable topsheet, a backsheet attached to said topsheet, and an absorbent structure positioned between said topsheet and said backsheet, said absorbent structure having a first wicking layer of wettable cellulosic fibers exhibiting a vertical liquid flux rate value at a height of about 15 centimeters of at least about 0.08 grams of liquid per minute per gram of absorbent structure per meter length of said first wicking layer, a second retention layer of a hydrogel-forming polymeric superabsorbent material, and a bonding agent for bonding said first wicking layer and said second retention layer to form a composite absorbent structure having a minimum contact intimacy ratio for providing a liquid transport function and a liquid retention function such that said first wicking layer and said second retention layer are combined together in a manner to obtain a contact to achieve liquid transport and liquid retention functions at a length of at least about 15 centimeters, a saturated capacity of at least about 5 grams of liquid per gram of composite absorbent structure, and an Absorbent Capacity at 15 cm of at least about 5 grams of liquid per gram of second retention layer.

19. The absorbent structure of claim 18, wherein said bonding agent comprises sheath/core polyethylene/polypropylene fibers.

20. The absorbent structure of claim 18, wherein said bonding agent comprises a polyaminoamide epichlorohydrin wet strength resin.

* * * * *

UNITED STATES PATENT AND TRADEMARK OFFICE
CERTIFICATE OF CORRECTION

PATENT NO.     : 6,329,565 B1
DATED          : December 11, 2001
INVENTOR(S)    : Dutkiewicz et al.

It is certified that error appears in the above-identified patent and that said Letters Patent is hereby corrected as shown below:

Column 2,
Line 66, change "FIG." to -- FIGURE --.

Column 3,
Lines 4, 7, 11, 14, 17 and 20, change "FIG." to -- FIGURE --.

Column 6,
Line 59, change "the the wettable" to -- the wettable --.

Column 7,
Line 45, change "(-1 cm to 1 13 cm)" to -- (-1 cm to -13 cm) --.

Column 9,
Line 9, change "Pat." to -- Patent --.

Column 11,
Line 13, change "Pat." to -- Patent --.
Line 43, change "FIG." to -- FIGURE --.
Line 46, change "FIGS." to -- FIGURE --.

Column 13,
Line 29, change "ST6" to -- STG --.

Column 14,
Lines 17 and 20, remove "-A) % STGPERPX.".
Lines 39 and 57, remove "XCENTROID % CAL. CONST.".

Column 15,
Line 9, remove "XCENTROID % CAL. CONST.".
Line 29, change "SANPLUS" to -- SAMPLUS --.
Line 34, change "HNEAM1" to -- HMEAN1 --.
Line 39, change "HNEAM2" to -- HMEAN2 --.
Line 45, remove "10.) % NUMERATR.".
Line 49, remove " "OF HEIGHT=", I.FRAME.H%".
Line 56, remove "INTIMACY{}".
Line 60, remove "PAIR ( )".
Line 68, add "Print """.

UNITED STATES PATENT AND TRADEMARK OFFICE
CERTIFICATE OF CORRECTION

PATENT NO. : 6,329,565 B1
DATED : December 11, 2001
INVENTOR(S) : Dutkiewicz et al.

It is certified that error appears in the above-identified patent and that said Letters Patent is hereby corrected as shown below:

Column 16,
Line 4, remove "LOCATION ( )".
Line 10, remove "LAYER ( )".
Line 31, change "FIG." to -- FIGURE --.

Column 24,
Line 48, change "FIG." to -- FIGURE --.

Column 26,
Lines 30 and 54, change "FIG." to -- FIGURE --.

Column 27,
Line 55, change "FIG." to -- FIGURE --.

Column 28,
Line 25, change "FIG." to -- FIGURE --.

Column 30,
Line 67, change "N.Y." to -- New York --.

Column 31,
Line 44, change "FIG." to -- FIGURE --.

Column 32,
Line 9, change "FIG." to -- FIGURE --.

Signed and Sealed this

Twenty-sixth Day of November, 2002

Attest:

JAMES E. ROGAN
Attesting Officer          Director of the United States Patent and Trademark Office

UNITED STATES PATENT AND TRADEMARK OFFICE
CERTIFICATE OF CORRECTION

PATENT NO. : 6,329,565 B1
DATED : December 11, 2001
INVENTOR(S) : Jacek K. Dutkiewicz et al.

It is certified that error appears in the above-identified patent and that said Letters Patent is hereby corrected as shown below:

Column 1,
Line 24, delete "wash" and substitute -- waste --.

Column 6,
Line 52, delete "agent combined together in" and substitute -- means in --
Line 27, delete insert -- means -- after "agent".

Column 7,
Line 19, delete "1 13 cm" and substitute -- 13 cm --.

Column 8,
Line 17, insert -- by removing terms relating to the missing third layer -- after "composite".

Column 9,
Line 12, delete ""g/min*gsm*inch"" and substitute -- (min x gasm x inch) --.
Line 14, delete "As used herein, the Vertical Liquid Flux rate value of a" and substitute -- Alternatively, this property may be reported in units of (g/min) X (m /g) which refers to grams of liquid per minute times vertical length (height) of first wicking layer per gram of wicking layer. 1.00 g/ (min x gsm x inch) = 39.4 (g/min) x (m /g). As used herein, the Vertical Liquid Flux of a --.
Line 19, delete "Vertical Liquid Flux rate" and substitute -- vertical liquid flux rate --.

Column 10,
Line 52, insert -- per unit -- after "layer".

Column 12,
Line 39, insert -- Reichert-Jung Polycut E (Leica Inc., Deerfield, Illinois, USA) -- after "the".

Column 13,
Line 11, delete" four low-angle incident flood lamps. The sample then is imaged with a 20 mm Leica Quantimet 970 Image Chalnicon scanner" and substitute -- transmitted light using an Olympus microscope Cleeds, Minneapolis, Minnesota, USA. The sample is then imaged with a 2' objective Chalnicon scanner, --.

UNITED STATES PATENT AND TRADEMARK OFFICE
CERTIFICATE OF CORRECTION

PATENT NO.   : 6,329,565 B1
DATED        : December 11, 2001
INVENTOR(S)  : Jacek K. Dutkiewicz et al.

It is certified that error appears in the above-identified patent and that said Letters Patent is hereby corrected as shown below:

Column 13 cont'd,
Line 18, delete "CONIM8" and substitute -- CONIM7 --.
Line 29, delete "ST6" and substitute -- STG --.
Line 33, delete "KRESSHER" and substitute -- KRESSNER --.
Line 59, delete "( X Y" and substitute -- (X Y X Y --.

Column 14,
Line 17, delete "-A) % STGPERPX" and substitute -- a * STGPERPX --.
Line 39, delete "XCENTROID % CAL.CONST" and substitute
-- XCENTROID * CAL.CONST --.

Signed and Sealed this

Sixth Day of May, 2003

JAMES E. ROGAN
*Director of the United States Patent and Trademark Office*